(12) United States Patent
Bachelder et al.

(10) Patent No.: US 10,471,703 B2
(45) Date of Patent: Nov. 12, 2019

(54) FACIAL MASK AND METHOD OF MAKING

(71) Applicant: Morpheus Medical Solutions, LLC, Duluth, MN (US)

(72) Inventors: Vance D. Bachelder, Duluth, MN (US); Jose Carrillo, III, Duluth, MN (US)

(73) Assignee: Morpheus Medical Solutions, LLC, Duluth, MN (US)

(*) Notice: Subject to any disclaimer, the term of this patent is extended or adjusted under 35 U.S.C. 154(b) by 638 days.

(21) Appl. No.: 14/640,542

(22) Filed: Mar. 6, 2015

(65) Prior Publication Data

US 2015/0250971 A1    Sep. 10, 2015

Related U.S. Application Data

(60) Provisional application No. 62/010,528, filed on Jun. 11, 2014, provisional application No. 61/950,591, filed on Mar. 10, 2014.

(51) Int. Cl.
*A61M 16/06*     (2006.01)
*B33Y 80/00*     (2015.01)
(Continued)

(52) U.S. Cl.
CPC .......... *B33Y 80/00* (2014.12); *A61M 16/0605* (2014.02); *A61M 16/0611* (2014.02);
(Continued)

(58) Field of Classification Search
CPC .......... A61M 16/0616; A61M 16/0605; A61M 16/06; A61M 2207/00; A61M 2016/0661;
(Continued)

(56) References Cited

U.S. PATENT DOCUMENTS 6,217,325 B1    4/2001    Chishti et al.
6,471,511 B1   10/2002   Chishti et al.
(Continued)

FOREIGN PATENT DOCUMENTS

CN        101861180 A    10/2010
WO        03105921 A2    12/2003
(Continued)

OTHER PUBLICATIONS

Grunewald, "Metamason Turns to 3D Scanning and 3D Printing to Customize the Respere CPAP Mask," 3D Printing Industry, Jul. 25, 2014. http://3dprintingindustry.com/2014/07/25/metamason-turns-3d-scanning-3d-printing-customize-respere-cpap-mask/.
(Continued)

*Primary Examiner* — Tan-Uyen T Ho
*Assistant Examiner* — Margaret M Luarca
(74) *Attorney, Agent, or Firm* — Seager, Tufte & Wickhem LLP.

(57) ABSTRACT

Masks for various uses and methods for manufacture thereof, including masks for use in continuous positive air pressure (CPAP) therapies. An example includes a mask having a first, relatively softer material for contact with the face of the user, and a second, relatively harder or more structural material used away from the face of the user, with a gradient therebetween. The mask can be produced by additive manufacturing to avoid a discernible boundary between the first and second materials.

4 Claims, 16 Drawing Sheets

(51) Int. Cl.
*B33Y 50/00* (2015.01)
*B29L 31/00* (2006.01)
*B33Y 10/00* (2015.01)
*B29L 31/50* (2006.01)
*B29L 31/48* (2006.01)
*B29C 64/112* (2017.01)

(52) U.S. Cl.
CPC ...... *B33Y 50/00* (2014.12); *A61M 2016/0661* (2013.01); *A61M 2207/10* (2013.01); *B29C 64/112* (2017.08); *B29L 2031/4835* (2013.01); *B29L 2031/507* (2013.01); *B29L 2031/753* (2013.01); *B33Y 10/00* (2014.12)

(58) Field of Classification Search
CPC .. B33Y 50/00; B33Y 80/00; B29L 2031/4835
See application file for complete search history.

(56) References Cited

U.S. PATENT DOCUMENTS

| | | | |
|---|---|---|---|
| 6,626,666 | B2 | 9/2003 | Chishti et al. |
| 6,705,863 | B2 | 3/2004 | Phan et al. |
| 6,722,880 | B2 | 3/2004 | Chishti et al. |
| 7,134,874 | B2 | 11/2006 | Chishti et al. |
| 8,070,487 | B2 | 12/2011 | Chishti et al. |
| 2005/0284478 | A1 | 12/2005 | Meyer et al. |
| 2006/0023228 | A1 | 2/2006 | Geng |
| 2006/0058632 | A1 | 3/2006 | McBurnett et al. |
| 2008/0006273 | A1* | 1/2008 | Thornton ............... A61M 16/06 128/206.21 |
| 2010/0009133 | A1* | 1/2010 | Chait ................... B29C 64/112 428/195.1 |
| 2011/0162654 | A1 | 7/2011 | Carroll et al. |
| 2012/0305003 | A1 | 12/2012 | Mark |
| 2014/0209098 | A1 | 7/2014 | Dunn et al. |
| 2014/0261430 | A1 | 9/2014 | Davis |
| 2014/0326243 | A1 | 11/2014 | Znamenskiy et al. |
| 2015/0265794 | A1* | 9/2015 | De Kruyff ............ A61M 16/06 128/200.23 |

FOREIGN PATENT DOCUMENTS

| | | |
|---|---|---|
| WO | 2008011682 A1 | 1/2008 |
| WO | 2009062265 A1 | 5/2009 |
| WO | 2013026091 A1 | 2/2013 |
| WO | 2014075797 A1 | 5/2014 |
| WO | 2014151324 A1 | 9/2014 |

OTHER PUBLICATIONS

"The Problem We Solve Obstructive Sleep Apnea (OSA)" Metamason, 2 pages, downloaded Jan. 28, 2015. http://www.metamason.com/#!better•cpap/cw4i.

"Respere." Metamason, 2 pages, downloaded Jan. 28, 2015. http://www.metamason.com/#!respere•by•rnetamason/c14qb.

"Metamason's Business Model" Metamason, 3 pages, downloaded Jan. 28, 2015. http://www.metamason.com/#!scan•fit•print/cj51.

Rucker, "NEUMA CPAP Mask," 2015.

Office Action for Application No. 201580024562.2, 13 pages, dated May 28, 2018.

\* cited by examiner

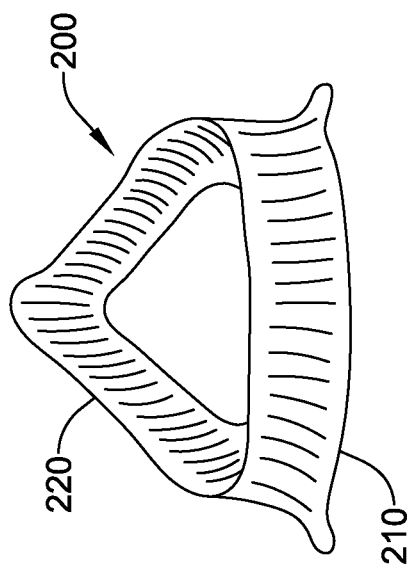
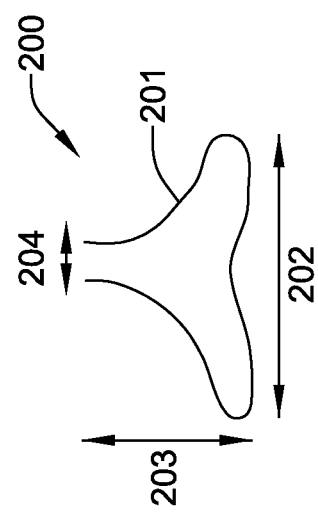
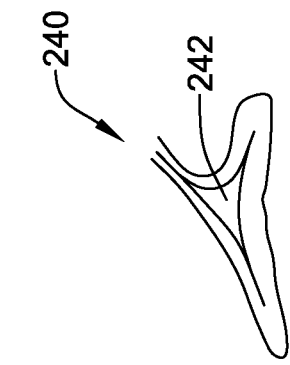
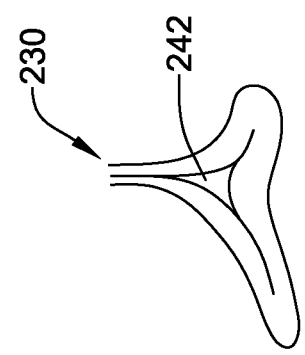
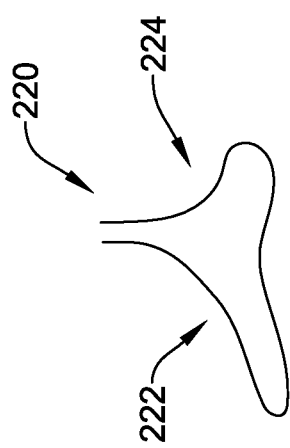
FIG. 3A
FIG. 3B
FIG. 3C
FIG. 3D
FIG. 3E

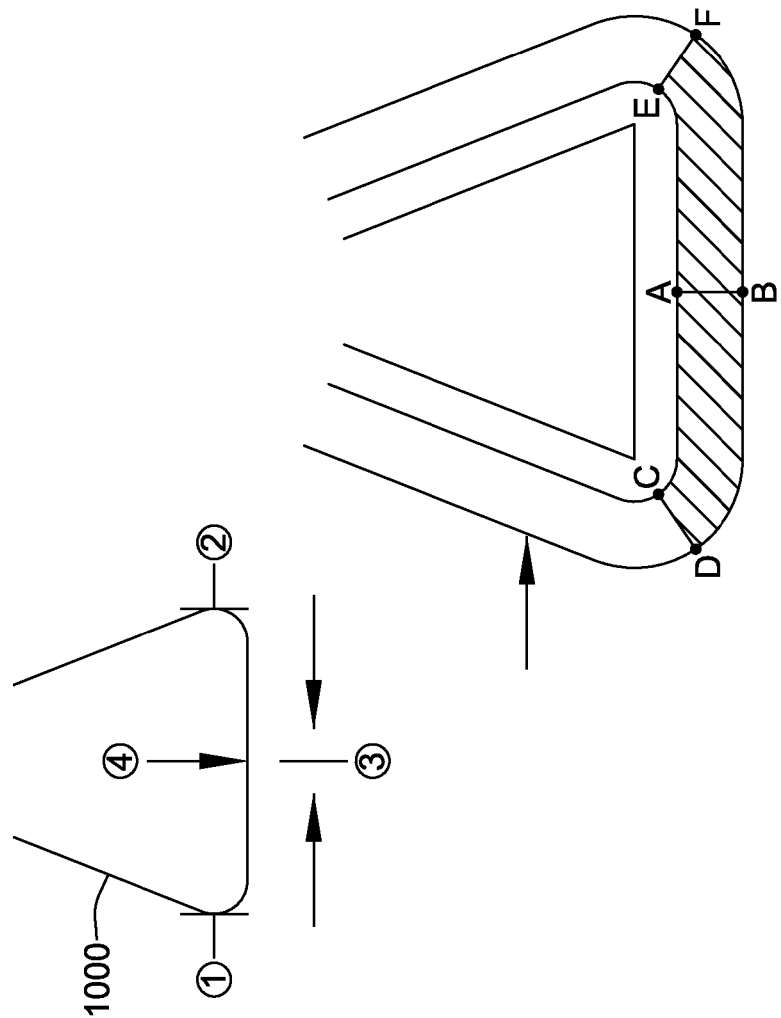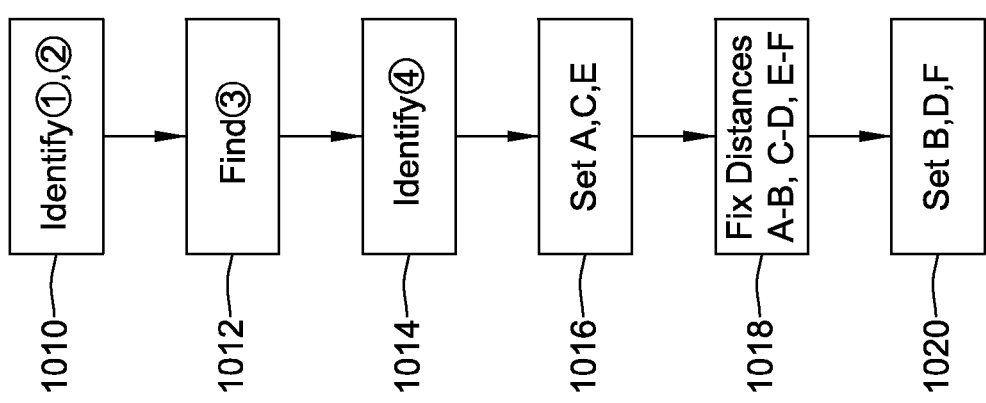
FIG. 15

FACIAL MASK AND METHOD OF MAKING

CROSS REFERENCE TO RELATED APPLICATIONS

The present application claims the benefit of and priority to each of U.S. Provisional Patent App. No. 61/950,591, filed Mar. 10, 2014 and titled FACIAL MASK AND METHOD OF MAKING, and U.S. Provisional Patent App. No. 62/010,528, filed Jun. 11, 2014, and titled FACIAL MASK AND METHOD OF MAKING, the disclosures of which are incorporated herein by reference.

BACKGROUND

Millions of people in the U.S. suffer from obstructive sleep apnea (OSA) with a prevalence of 20-30% in men and 10-15% in women. OSA is a condition where the upper airway collapses during sleep and significantly limits or obstructs air entry into the lungs. The mainstay of treatment for OSA is continuous positive airway pressure (CPAP). This works by simply applying positive air pressure to the upper airway which consists of the nasal passages, mouth, nasopharynx, oropharynx, and hypopharynx. CPAP pressure opens the upper airway, allowing the sleeper to breathe easily without intermittent obstruction and interruption of airflow into the lungs.

CPAP pressure is delivered via a mask applied over the nose (nasal mask) or over the nose and mouth (full face mask) with air pressure tubing running from the mask to a CPAP machine. A good mask seal is desirable as high leak rates from air escaping around the sides of the mask are uncomfortable and may disrupt sleep. High leak rates may also cause CPAP treatment to be ineffective.

Some sleepers find using a mask at night uncomfortable and so have difficulty sleeping with one. Further, some sleepers will easily fall asleep using a CPAP mask only to discover that sometime during the night it has come off or that they have removed it surreptitiously. These problems clearly make CPAP therapy less effective than it otherwise might be.

A process whereby a more comfortable and effective mask with lower leak rates could be easily manufactured would be a great advancement in the treatment of OSA and other forms of sleep disordered breathing.

Such an advancement would also benefit the manufacture of other medical masks and certain other medical facial apparatus such as oxygen masks used for surgery and in recovery, masks used for delivery of gaseous medicaments, and the like such as for dental or surgical procedures; "nasal pillows", circumferential fittings for the nasal inlets; additionally, non-medical masks such as snorkeling or diving masks would benefit from increased comfort and a better seal, which would lower the egress rate of water into the mask during use.

Such an advancement would also benefit the manufacture of other articles where differential pressure in contact with the human or animal body can cause discomfort.

OVERVIEW

The present inventor has recognized, among other things, that a problem to be solved includes the provision of masks for various uses including CPAP having gradual transitions from one material property to another. Several solutions to this problem may be realized by embodiments shown below, some of which can be fabricated by the use of facial imaging and three-dimensional printing ("3D Printing").

A first example takes the form of a facial mask comprising a first material and a second material and a material gradient in at least a portion of the mask, the material gradient transitioning from the first material to the second material. A second embodiment is a facial mask as in the first example, wherein the first material is a polymeric material suited to a first purpose, and the second material is a polymeric material suited to a second purpose and not to the first purpose. A third example takes the form of a facial mask as in either of the first two examples, wherein the first material is a relatively softer material well suited to contact with the face of a patient, and the second material is a harder material well suited to providing a structure and shape to the mask.

A fourth example is a facial mask as in any of the first three examples further comprising two or more gradients. A fifth example is a facial mask as in any of the first four examples, wherein the first and second materials differ in one or more of modulus, elasticity, glass transition temperature, degree of crystallinity, ductility, softening point, or melt flow index. A sixth example is a facial mask as in any of the first five examples, wherein the mask is a CPAP mask. A seventh example is a facial mask as in any of the first six examples, wherein the mask is made by additive manufacturing without the use of insert molding or casting.

An eighth example is a facial mask as in any of the first seven examples wherein the material gradient or gradients are characterized by a lack of discernible boundary insofar as there is no visible boundary to the naked eye. A ninth example is a facial mask as in any of the first eight examples wherein the material gradient or gradients are characterized by a lack of discernible boundary insofar as a boundary cannot be identified under manual inspection.

A tenth example takes the form of a method of manufacturing a facial mask, the method comprising obtaining a set of facial contours of a person's face by one or more of digital photography, video, infrared, or laser scanning; optimizing a set of mask contours for an area where a mask will come in contact with the person's face; and constructing a mask using an additive printing process including a first layer of a first material having first properties and a second layer of a second material having second properties and a material gradient between the first and second layers in at least a portion of the mask, the material gradient characterized by the lack of a discernible boundary between the first and second materials.

An eleventh example is a method as in the tenth example wherein the constructing step is performed such that the first material is a polymeric material suited to a first purpose, and the second material is a polymeric material suited to a second purpose and not to the first purpose. A twelfth example is a method as in either of the tenth or eleventh examples wherein the constructing step is performed such that the first material is a relatively softer material well suited to contact with the face of a patient, and the second material is a harder material well suited to providing a structure and shape to the mask. A thirteenth examples is a method as in any of the tenth to twelfth examples wherein the constructing step is performed by introducing a third material having third material properties different from each of the first and second materials and joining the third material to at least one of the first and second materials using at least a second gradient characterized by a lack of discernible boundary to the first and/or second materials.

A fourteenth example is a method as in any of the tenth to thirteenth examples, wherein the constructing step is performed using first and second materials that differ in one or more of modulus, elasticity, glass transition temperature, degree of crystallinity, ductility, softening point, or melt flow index. A fifteenth example is a method as in any of the tenth to fourteenth examples wherein the constructing step is performed without the use of insert molding or casting. A sixteenth example is a method as in any of the tenth to fifteenth examples wherein the additive process is performed such that the material gradient is characterized by a lack of discernible boundary from the first material to the second material insofar as there is no visible boundary to the naked eye from the first material to the second material.

A seventeenth example is a method as in any of the tenth to sixteenth examples wherein the additive process is performed such that the material gradient is characterized by a lack of discernible boundary from the first material to the second material insofar as a boundary cannot be identified under manual inspection. An eighteenth example is a method as in any of the tenth to seventeenth examples wherein the step of optimizing a set of mask contours comprises identifying one or more fiducial points of the set of facial contours associated with one or more of the patient's nose, lips, or eyes and setting an inner boundary and an outer boundary relative to the identified fiducial point or points.

A nineteenth example takes the form of a continuous positive air pressure facial mask for the treatment of sleep apnea built according to a method as in any of the tenth to eighteenth examples.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 3A-3E show several designs for nasal masks;

FIG. 15 shows an illustrative example of the selecting of inner and outer boundaries based on identified fiducial points.

DETAILED DESCRIPTION

Figure 1:
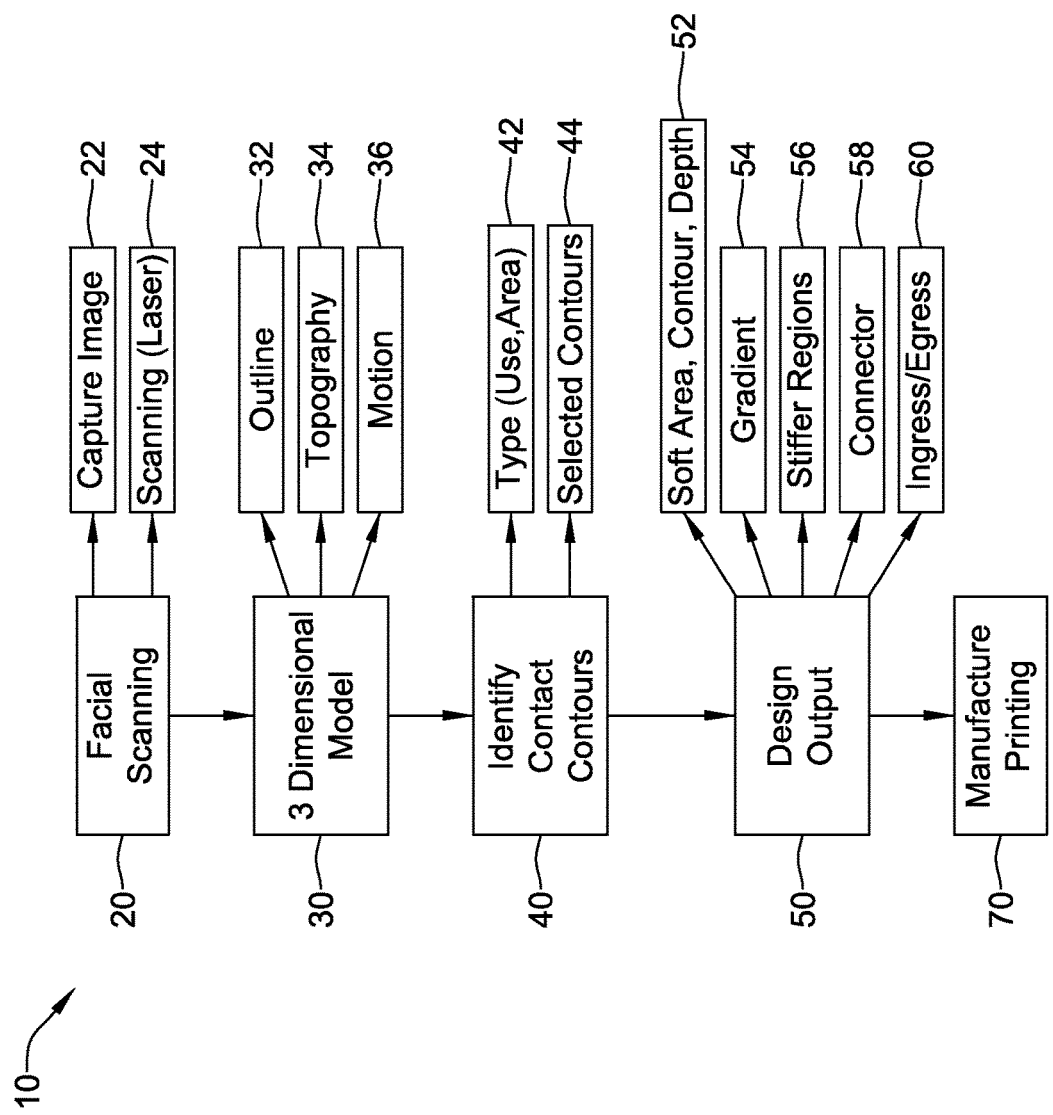
FIG. 1 is a flow chart for an illustrative method.

Although the present disclosure provides references to preferred embodiments, persons skilled in the art will recognize that changes may be made in form and detail without departing from the spirit and scope of the invention. Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

Described herein are a series of mask or orthotic articles, related by the common principle that the articles are formed to contact the surface of a human or animal body. In some embodiments, articles are characterized by one or more material gradients incorporated integrally within the article for the purpose of providing increased comfort, better fit, and the like. A gradient includes at least two different materials having distinctly different material properties such as modulus, ductility, and the like, wherein the materials are changed over from at least first to second relative compositions without a discernible boundary therebetween. Hence, as used herein, the term "gradient" means having a substantial lack of a discernible boundary or interface between areas of different composition. For example, a gradient may span from a first region substantially made of a first material to a second region substantially made of a second material, with the gradient gradually transitioning (in stepwise or continuous manner) from the first material to the second material, without a discernible boundary. In another example, a gradient may span from a first region of a first blend of materials to a second blend of materials, with the gradient gradually transitioning (in stepwise or continuous manner) from the first blend to the second blend, without a discernible boundary. The articles described herein have non-gradient regions and gradient regions in some embodiments. In some embodiments, the articles have two or more gradient regions. Gradients include both linear gradients and non-linear gradients.

Gradient articles can be suitably formed using a 3D printer employing two or more materials that are capable of providing different properties such as modulus, ductility, and the like. In some embodiments, the materials delivered are UV curable compositions that are delivered, or printed, in substantially liquid form, then solidified by UV irradiation that initiates one or more polymerization and/or crosslinking reactions in the printed compositions. Fine structures can be suitably formed with mixtures of materials at continuously changing ratios, which in turn leads to a material gradient. Gradient changes may be stepwise as well, with the intention being that the steps occur without discernible boundary to a user viewing an article or portion thereof with the naked eye or manually inspecting an article or a portion thereof. Computer algorithms aid in determining the proper ratios of materials to provide the desired gradient. Such gradients are suitably linear or nonlinear, monodirectional or multidirectional (horizontal, vertical, radial, or more than one of these).

Increased comfort can be achieved for articles contacting the human body when gradient differences are employed, when compared to similar articles that employ a blend of materials wherein no gradient between materials is present.

Additionally, providing a gradient of materials reduces the wear and tear that occurs at sharp interfaces and boundaries where the article is subjected to relatively high stress, rapid movement, or both. These and other benefits of providing material gradients in articles that contact the human body surface will be readily apparent through the description of several specific examples. The examples described below are intended to be only representative of many embodiments that are possible, as will be appreciated by one of skill in the art.

Described herein is a method of fabricating custom-made CPAP masks, and a custom-made mask that includes one or more material gradients. Fabricating a CPAP mask that conforms to the shape of a sleeper's face decreases leak rates, improves comfort, and allows for less respiratory dead space, and requires less material for manufacture of the mask itself. Provision of material gradients provides for increased comfort and improved fit in areas of the mask by controlling pressure distribution where differential pressure during contact of the mask with the face would otherwise cause discomfort.

The method of manufacture incorporates the use of facial scanning techniques (pictures, video, laser scanning, etc.) to define a surface as the basis for crafting a CPAP mask using a 3D printer. Use of 3D printing, also referred to as additive manufacturing, incorporates additional benefits such as elimination of material waste during manufacturing and quick fabrication of customized articles of manufacture.

The mask of an illustrative example incorporates at least two different materials having distinct material properties such as modulus and ductility, wherein the materials are changed over in one or more seamless gradients. One company, Metamason, has discussed using a 3D scan of the patient's face in order to generate molds that can be used to fabricate custom masks. However, this process requires the 3D scan to be transmitted to a fabrication plant where the molds for a mask are made using 3D printing, and masks are made using a combination of molding and casting processes. A simpler process would be to generate the masks directly by the use of 3D printing. The material gradients may be incorporated into the mask through a portion of the thickness of the mask or the entirety of the thickness of the mask; or across a horizontal direction (when the mask is situated on the patient's face and the patient is standing or sitting upright) or a portion of a horizontal direction; or across a vertical direction or portion of a vertical direction. Combinations of any of these are suitably combined and multiple gradients in a single direction, or combination of directions, are incorporated into the masks of the invention. Further, a gradient combines in some embodiments more than two different materials. For example, a single gradient may proceed, in a selected direction, from a first material composition to a second material composition and finally to a third material composition. Various materials are suitably included in different gradients, wherein the type of gradient is determined by the customized fit required.

While not particularly limited as to the number of materials employed in the gradient, in some embodiments two or more materials having different properties of modulus, elasticity, glass transition temperature, degree of crystallinity, ductility, softening point, melt flow index, and the like or two or more different material properties are employed in the gradients imparted to the masks. In some embodiments, three or more materials, for example up to ten different materials, or four to seven different materials, are suitably employed.

In some embodiments, the transition between materials over the gradient is rapid over a selected distance; in other embodiments the transition between materials is gradual within the same distance. In general, the one or more gradients are characterized by the lack of a discernible boundary between materials, where the boundary is not seen with the naked eye or apparent upon physical/tactile inspection. A structure formed in an additive process where material composition and/or properties change from one location to another of the article can include gradients by avoiding abrupt transition. In contrast, an insert molded piece, for example, will generally have a non-gradual, and non-gradient, transition at the borders of the insert piece and the molding material. The inclusion of peripheral or secondary elements which are adhered or bonded to an article which incorporates a gradient transition does not negate the gradient nature of the article which has the gradient transition. For example, as also discussed below, some embodiments include a mask foot having gradient transitions from softer to firmer or more structural materials, while also including a separate cap or port which is attached in a subsequent bonding step. Such embodiments include a gradient structure even though there is also one or more abrupt transitions.

The one or more material gradients are suitably applied employing additive manufacturing using a printer that is capable of printing two or more materials having different properties. In some embodiments, the materials are added by melting the materials and allowing solidification after application of a printed layer. In other embodiments, a liquid or syrup of curable materials are applied as printed layers and each layer is cured to result in a solid polymer prior to application of a subsequent layer. In some such embodiments, crosslinking of one or more materials is also accomplished, wherein degree of crosslinking is suitably controlled by functionality of the liquid or syrup applied in each layer or the treatment (irradiation, for example) of each layer.

In some embodiments, the additive manufacturing is carried out wherein blends of two or more materials are suitably formed prior to deposition. Thus, where a gradient is desired, mixing ratios of two or more materials may be adjusted with each addition of a layer to result in the desired gradient of deposited material. It will be appreciated that two, three, or more different materials may be suitably included in a blend for any given area of addition to give the manufacturer complete control over the material gradient.

Additive manufacturing provides customization for maximum patient comfort, while the gradients enable control of rigidity of the mask. These features are highly beneficial for any type of facial mask, other types of masks, such as oxygen delivery masks or masks used for resuscitation or anesthesia applications or snorkeling/diving masks.

Another use of seamless compliant gradients may include the use of small amounts of harder (higher modulus, lower ductility, or both) materials to form the skeleton of the mask that would also include softer (lower modulus, higher ductility, or both) materials. This approach incorporates a horizontal gradient of materials to create a customized distribution of pressure at the area of skin contact while using a variety of shapes to make that contact. This may result in better comfort and safety while using the mask.

In terms of clinical benefit, softer materials at skin contact with customized gradients transitioning to stiffer materials both in the vertical and horizontal directions as well as through mask thickness provides both excellent fit and control of pressure distribution at the skin-mask interface. Customized pressure distribution results in improved mask performance combined with improved comfort. Improving patient comfort leads in turn to better mask tolerance and better compliance with treatment recommendations.

A further advantage of the invention is that the masks can be printed with customizable color options incorporated. Thus, custom decorations or logo designs are easily incorporated in the mask. Yet another advantage of the invention is that the process overall is easy for any physician and patient to use without the need for cumbersome molds or facial impressions, and provides a rapid progression from facial scanning/measurement to finished mask. For some implementations, another advantage of the invention is that no inventory needs to be stored; each mask is made on demand, so only a supply of materials for printing need to be kept at the manufacturing site.

FIG. 1 shows a flow chart for an illustrative method of making a customized facial mask. The illustrative begins at block 20, where a person's face is scanned by one or more techniques including digital photography, video, laser scan, and the like in a manner that captures the contours of the patient's face. For example, an image may be captured, as indicated at 22 using photography or video capture. Alternatively, as shown at 24, a scanning or interrogation system may use laser or other imaging system to scan the surface contours of a patient. Subsurface characteristics may also be captured by using multiple imaging modalities, so that areas of tissue with bone and cartilage may receive different treatment in the final mask design, by providing, for example, softer or firmer materials in those regions, than areas of softer tissue having subcutaneous fat or muscle. A physician input may be used in block 20 as well to generate fiducial points in the captured scan or image, for example, identifying the edges of the lips and eyes, nostrils or other points of possible interest, to facilitate a mapping of areas of greater and lesser likely patient movement, tissue softness/hardness, etc.

Using the inputs gathered during facial scanning 20, a three-dimensional (3D) model of the patient's face is generated at block 30. The 3D model may include an outline of areas of interest, as indicated at 32, which may be generated directly from captured or scanned data, or may include physician inputs. The facial topography 34 including surface contours and areas identified as (or determined by use of multiple imaging modalities) firmer or softer tissue may be identified. Areas of potential motion 36, for example near the lips or eyes, may also be mapped.

Next the contours of facial contact are identified in block 40. These areas may be determined by (optionally) first noting the type of mask to be formed at 42, for example, whether a full-face mask or nasal mask for CPAP, a mask for other medical purposes (an oxygen mask), or a mask for watersports (snorkeling or diving). Element 42 is optional; some embodiments will be dedicated to a single purpose—that is, the physician's office may simply make a single type of CPAP mask and have no need to make, for example, a diving mask. Using this input 42, the method then selects the contours of facial contact from the 3D model, as indicated at 44.

The method then includes generating a design output, as indicated at 50 the design output 50 may include mapping of areas of softer areas, the contour of the tissue interface, the depth or thickness of materials as shown at 52, as well as gradients 54 to use in transitioning from softer to stiffer regions 56 and the mapping of stiffer regions. The design output may include features to facilitate or include a connector 58. The design output may also include manufacturing details related to whether the mask is intended to prevent ingress of water, as in for watersports, or egress of pressurized air, as would be the case for a CPAP mask, as indicated at 60. The design may be different based on block 60 by, for example, providing an inward flare at the tissue interface to prevent air egress, or an outward flare at the tissue interface to prevent water ingress. It is noted that the design output 50 for an illustrative embodiment includes both softer areas contoured for tissue contact 52 and harder or stiffer regions 56 to maintain overall shape and structure, with one or more seamless gradients 54 therebetween.

Finally, as indicated at 70, the mask is manufactured, preferably by a 3D printing process. Next, the mask may be cured, cleaned and/or sterilized, as fits the needs of the application and user. The mask may then be provided to its user.

Figure 2:
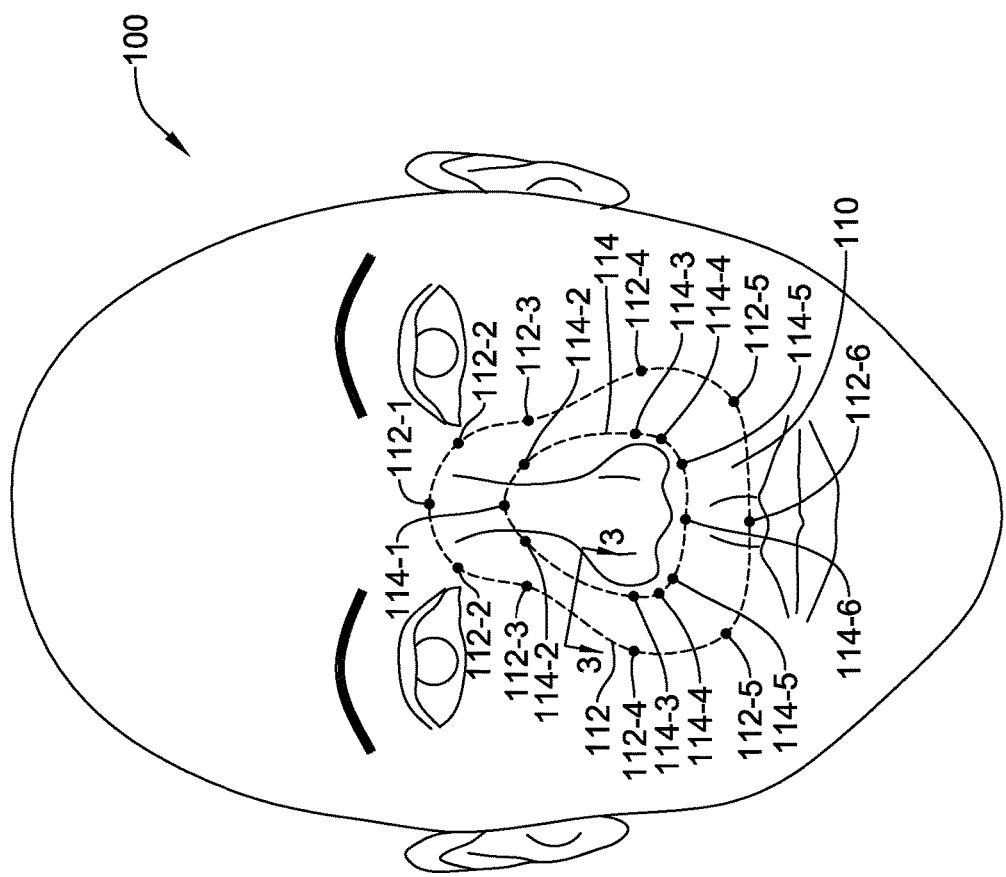
FIG. 2 illustrates a patient wearing a nasal mask.

FIG. 2 is a schematic view of a mask contact surface 110 situated on a scanned face 100 to show how the anatomical points of the face 100 are used to define an outer boundary 112 and inner boundary 114. Mask contact surface 110 is shown as defined by several points in reference to face 100.

Outer boundary 112 is defined by point 112-1 (4 mm below the nasion), point 112-2 (2 mm medial to the crunc lacrim), point 112-3 (6 mm lateral from the rhinion), point 112-4 (7 mm lateral to the alar facial groove), point 112-5 (superior to the corner of the mouth and resting on the nasolabial fold), and point 112-6 (1 mm above the vemillion border at the midline). Inner boundary 114 is defined by point 114-1 (2.4 mm below the nasion), point 114-2 (1 mm lateral to the rhinion), point 114-3 (1 mm lateral to the alar sidewalls), point 114-4 (1 mm inferior to the termination of the alar sidewalls), point 114-5 (midway between points 114-3 and 114-4 and 1 mm lateral to the alar sidewalls), and point 114-6 (midline 1 mm below the columell-labial angle). These points collectively define an outer boundary 112 and an inner boundary 114 that may be smoothed using a "best curve fit" algorithm. This will ensure smooth curvature of the defining boundary lines. These specific distances are merely illustrative and may vary.

These points 112-1 through 112-6 and 114-1 to 114-6 may be identified by any suitable manner. For example, the facial imaging may automatically generate these points by, for example, identifying bony structures during facial imaging itself, for example by overlaying an X-ray image or thermal imaging with a visible image. In an alternative, the physician may place stickers or use a marker to create dots, for example, at specific points on the patient's face prior to imaging to enable one or more fiducial points to be identified. The points may also be auto-generated by finding fiducials at the edges of the eyes, nose and/or lips.

The area between the inner and outer boundary lines of FIG. 2 defines the skin contact surface of the mask. The contact surface mask is thus identified on the computer generated 3D facial surface and is designed to have features matching the inverse contours of the facial surface. The embodiment of FIG. 2 identifies a mask contact surface 110 that is 2 cm over the bridge of the nose at its widest and 0.7 cm lateral to the nasion. It will be understood by those of skill that these and other dimensions will fluctuate from a mask to mask depending on individual facial anatomy of the user.

The contact surface of the mask contacts the patient's face within the boundaries described with respect to FIG. 2 and has a three-dimensional shape, referred to herein as the mask foot, that proceeds in a perpendicular direction from the facial area to contact the remainder of the mask, referred to herein as the mask body. The mask foot is tapered as it proceeds from the facial contact surface toward the mask body. One or both of the mask foot and the mask body may include material gradients to provide a gradient of modulus in one or more directions. The material gradients are characterized by the substantial absence of distinct interfaces.

FIG. 3A shows one example of a cross section 201 of a lower portion of a mask foot 200, taken along line 3-3 of FIG. 2. The cross section 201 is a generally triangular shape with concave sides allowing for reduction in materials use while allowing for greater surface area contact. The sides of the cross section 201 follow the form of a hyperbola of the equation y=1/x as defined by Cartesian coordinates. The base (skin contact area) may follow the shape of an inverted parabola of the equation $$y=-x^2$$

where x is defined between −0.25 and 0.25. This will give the foot a cross sectional shape approximated by FIG. 2A. Thus, the cross section 201 has base length 202 of 0.7-2.0 cm, height 203 of 1.0 cm, and apex width 204 of 0.2 cm.

Extending the foot cross section of FIG. 3A to a 3-dimensional form results the shape approximated in FIG. 3B. FIG. 3B shows a mask foot 200 that would form the basic seal for the mask that would extend around the nose, having base area 210 and apex area 220. Base area 210 contacts the face during use. In some embodiments, the materials used to form mask foot 200 of FIG. 3B having cross section 201 of FIG. 3A include two different materials that are printed then cured using UV light, such that a gradient of the two materials are formed. In some such embodiments, the base 210 of FIG. 3B consists essentially of 100% Tango Plus FLX930 with Shore A hardness of 26-28 after cure, and transitions in a substantially linear gradient from base 210 to apex 220 wherein apex 220 consists essentially of 100% VeroClear RGD810 having a Shore D hardness after cure of 83-86. Both Tango Plus FLX930 and VeroClear RGD810 are commercial photopolymers for 3D printing available from Stratasys; other materials may be used. The elasticity modulus of TangoPlus is estimated around 150-300 MPa while the elasticity modulus of VeroClear is 2000-3000 MPa. Thus, the elasticity modulus at 0.5 cm base height, or ½ total foot height, is approximately 1200 MPa. In this embodiment, the gradient transition is affected from base to apex. Other materials and gradient designs are also envisioned.

This gradient transition from base to apex of the mask foot yields a substantial improvement in comfort and fit. However, one of skill will envision modifications to the basic form shown in FIGS. 3A, 3B that would allow for further improvements. For example, rather than a symmetric foot cross sectional shape, an elongated asymmetrical cross section such as that shown in FIG. 3C would reduce the overall dead space within the mask and allow for the body of the mask to settle closer to the skin surface when in use. FIG. 3C shows an asymmetry between first side 222 of cross section 220 and second side 222 of cross section 220. During use, first side 222 of a 3-dimensional mask foot based on cross section 220 faces the external side of the mask, while second side 222 faces the interior of the mask. The asymmetrical design of FIG. 3C has the same baseline as the mask foot 200 shown in FIGS. 3A, 3B but the apex is shifted medially and centered at 30% of the total width as measured starting from the midline edge of the foot cross section 220. The concave arcs of the foot medially and laterally are defined using the apex line as the Y axis and the base as the X axis and using hyperbolic forms as noted above. In this design, the pressure exerted by the mask upon the skin may be more localized medially.

Uneven pressure distribution caused by the use of cross section 220 of FIG. 3C may be overcome by the use of a core skeleton that would distribute such pressure evenly along the base of the foot. The basic shape of this designs is shown in FIG. 3D, wherein cross section of mask foot 230 includes core skeleton 232. In some embodiments, core skeleton 232 is printed during manufacture, for example by printing a third material while the two gradient materials are printed and cured to substantially surround core skeleton 232. In other embodiments, core skeleton 232 consists essentially of 100% VeroClear RGD810 throughout, wherein the core skeleton 232 is present within the otherwise linear gradient as described for mask foot 200. Alternatively, core skeleton 232 is a member, such as a metal member, that is placed in the print area and the two gradient materials are printed and cured so as to surround the core skeleton 232.

In another modification, the core skeleton configuration of FIG. 3D includes a modulus gradient proceeding from exterior to interior, instead of or in addition to the modulus gradient traveling from base to apex. In one such embodiment, the core skeleton consists essentially of VeroClear and is situated approximately 1 mm below the surface of the mask foot. A "skin" consisting essentially of 100% TangoPlus covers the entirety of the mask foot at a depth of 1 mm from the surface. A linear gradient proceeds from 100% TangoPlus to 100% VeroClear over a 1 mm distance towards the interior of the mask foot. This suggests that the elasticity modulus at a depth of 1.5 mm below the mask surface in any direction would approximate 1200 MPa.

Another mask foot modification that is particularly advantageous from a cosmetic and materials use standpoint is employing a modified mask foot shape in the area of the mask foot that contacts the bridge of the nose. This modification calls for extending the mask foot at the "ankle" so that the apex runs inferiorly and more closely to the anatomic nose, reducing the amount of material needed and giving a more pleasant aesthetic look and feel. This modified mask foot profile is shown in FIG. 3E.

In FIG. 3E, the core skeleton 242 of mask foot 240 is the same as of FIG. 3D above. However, the concave shape of the mask foot arising from the outer boundary will follow a curve defined by the portion of a hyperbola of y=1/x where x is between 1 and 3. The concave portion of the mask foot arising from this inner boundary will be defined the parabola $y=x^2$ where the y axis is defined by two points, the first point where the mask foot base and mask foot outer surface meet and the second point is any point along the arc equidistant between the angle defined by the line described by the base of the mask foot and the line described by the point of outer and base surface contact and the outer apex termination point. In some embodiments, the modified mask foot profile of FIG. 3E includes a modulus gradient proceeding from exterior to interior, wherein a "skin" consisting essentially of 100% TangoPlus covers the entirety of the mask foot at a depth of 1 mm from the surface. A linear gradient proceeds from 100% TangoPlus to 100% VeroClear over a 1 mm distance towards the interior of the mask foot. This suggests that the elasticity modulus at a depth of 1.5 mm below the mask surface in any direction would approximate 1200 MPa.

These modifications are useful in various combinations. For example, a mask foot that incorporates both the designs described in FIG. 3C and that described in FIG. 3E may be suitably employed in a single mask foot. Use of such a design increases the performance of the mask in avoiding leaks, because mask leaks are known by those of skill to occur primarily over the bridge of the nose and, when using a full face masks that cover both nose and mouth, over the soft portions of the cheek. Thus, in some embodiments, a nasal mask that incorporates mask foot design of FIG. 3E over the bridge of the nose and mask foot design of one of FIG. 3A, FIG. 3C or FIG. 3D, or a combination of two or more thereof for the remainder of the mask contact area is suitably employed.

Figure 4:
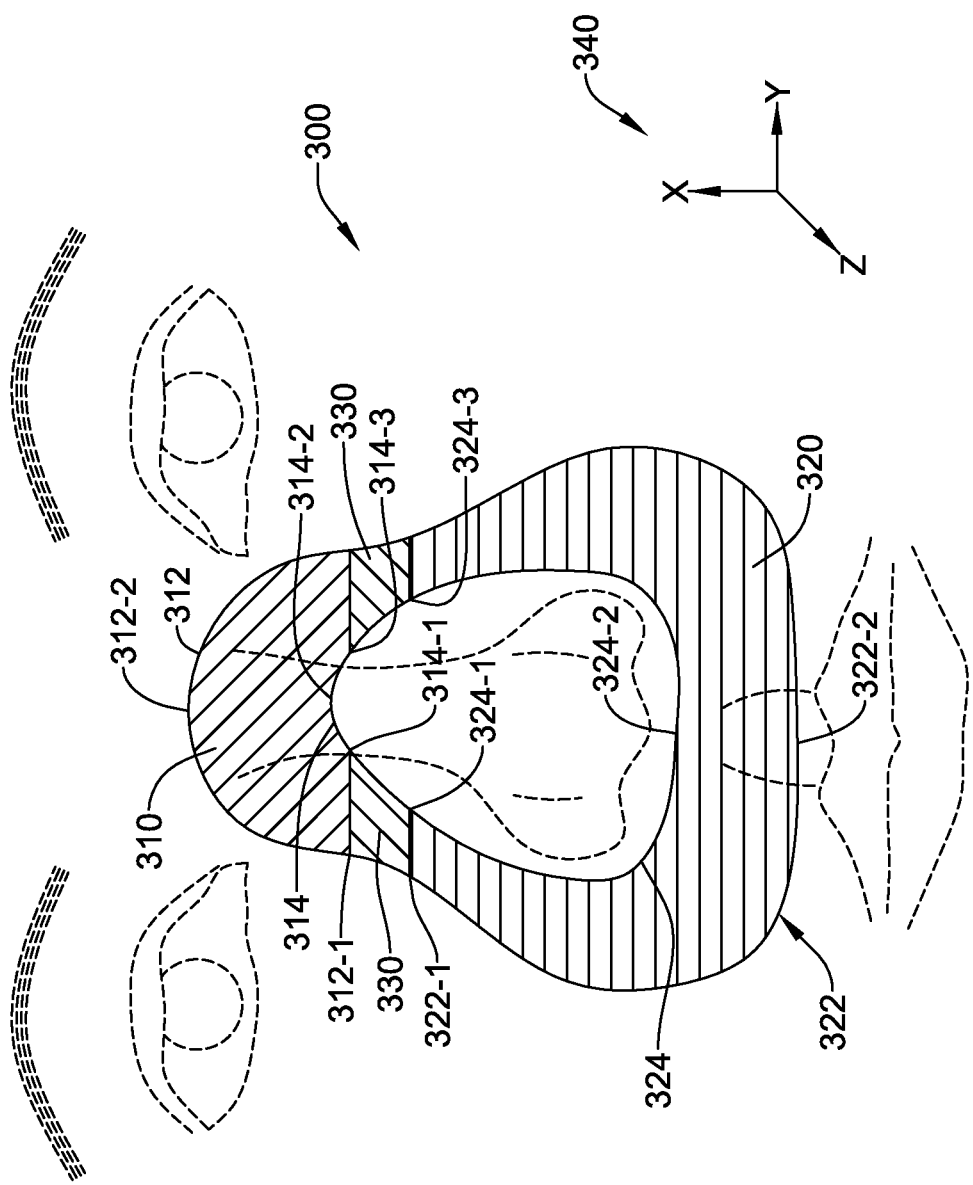
FIG. 4 illustrates a patient wearing another nasal mask.

FIG. 4 shows one embodiment of a combination mask design. Referring to FIG. 4, the mask foot design of FIG. 3E is employed in mask 300 over an upper zone 310 having outer boundary 312 and inner boundary 314 and defined by the outer curve running from first outer boundary point 312-1 through second outer boundary point 312-2 to third outer boundary point 312-3, inner curve running from first inner boundary point 314-1 through second inner boundary point 314-2 to third inner boundary point 314-3, and by the lines running from first outer boundary point 312-1 to first inner boundary point 314-1 and from third outer boundary point 312-3 to third inner boundary point 314-3. In some embodiments, upper zone 310 is includes a material gradient proceeding from exterior to interior as described for FIG. 3E.

Further in the illustration of FIG. 4, the mask foot design of FIG. 3C is employed in lower zone 320 having outer boundary 322 and inner boundary 324 and defined by the outer curve running from first outer boundary point 322-1 through second outer boundary point 322-2 to third outer boundary point 322-3, inner curve running from first inner boundary point 324-1 through second inner boundary point 324-2 to third inner boundary point 324-3, and by the lines running from first outer boundary point 322-1 to first inner boundary point 324-1 and from third outer boundary point 322-3 to third inner boundary point 324-3. In some embodiments, lower zone 320 is characterized by a material gradient proceeding from base to apex as described for FIG. 3B.

For the embodiment in FIG. 4, transition zones 330 are defined by the areas described by the four first boundary points (312-1, 314-1, 322-1, and 324-1) and the four third boundary points (312-3, 314-3, 322-3, and 324-3). In this embodiment, the transition zones 330 provide a transition or gradient between the design of FIG. 3E, and the design of FIG. 3C. Such a transition or gradient can proceed from the inclusion of a core skeleton in upper zone 310 to the absence of a core skeleton in lower zone 320. However, in some embodiments, the transition zones 330 have no core skeleton element; in other embodiments, transition zones 330 have a core skeleton element that ends at the end of the transition zone. In any of these embodiments, transition zones 330 may include a material gradient aside from the presence or absence of a core skeleton element.

In this example of FIG. 4, gradients may operate in all three directions, X, Y and Z, as indicated at 340. In the X direction, at least the transition zone 330 may be stiffer closer to the bridge of the nose than it is closer to the nostrils. In the Y direction, the inner and outer edges of the lower zone 320 may be more flexible than the center portion thereof in one or more layers. Finally, in the Z direction, the overall mask 300 may be softer at the tissue interface than it is away from the patient's skin.

The material gradient of transition zones 330 of FIG. 4 is designed and adapted to provide a smooth transition between the material gradients selected for the upper zone 310 and lower zone 320. Thus, in the example set forth in FIG. 4, the material gradient transitions from the exterior-to-interior gradient of upper zone 310 to the bottom-to-top gradient of lower zone 320. Additionally, the shape of the mask foot cross section is transitioned, in the embodiment shown in FIG. 4, from the cross section shape 240 of FIG. 3E to the cross section shape 220 of FIG. 3C. Such transitions may be effected within the directions for the 3D printing by varying the material composition from one position to another of the printer output. The output may be varied continuously or in steps such that a single mask 300 may have various zones with differing material properties, with at least two of the zones meeting across a gradient transition.

It is an advantage for some embodiments of the present invention that two or more material gradients are applied in a single construction such as that described in detail for FIG. 4. It is a further advantage that transition areas between zones having different material gradients, different shapes, or both are easily provided.

Once the description of the mask foot has been computationally rendered, the remaining body of the mask will be formed. The mask body may be formed by considering the topical geography of the face already described by initial computer surface modeling. In some embodiments, on the other hand, since the mask body is separated by the mask foot from the patients face, the mask body can be standardized to the overall size of the patient's face, rather than being unique to the patient.

In some embodiments, the facial contact surface is further defined by the outer edge of the circumferential line formed by the apex of the mask foot as shown in FIGS. 3A-3E, and in other embodiments a different mask foot having a different apex thickness is employed. This region may have a thickness in the range of 1-4 mm, with 2 mm preferred. The modeled surface may be trimmed electronically or automatically to the desired shape.

Where the mask is a CPAP mask, a standard tubing attachment port is added with the lowest circular edge approximately 6-10 mm above the interior edge of lowest point of the mask foot and preferably centered within the mask construction. The mask body in some embodiments may be separately fabricated, with the tubing attachment port integral to the mask body which can then be attached to the mask foot by adhesive, heat or other process. In another embodiment, the mask body can be overmolded onto the mask foot, with a location for a tubing port built into the overmold. In yet another embodiment, the mask body and mask foot are 3D printed as one, with space left for the tubing port at an appropriate location. In some embodiments, the mask body is formed entirely of a low modulus material, such as cured VeroClear RGD810, with no material gradient in the mask body, though the transition from the softer mask foot to the mask body may include a gradient of higher and lower modulus materials.

A full face mask design is also easily envisioned using the specific parameters set forth above for FIGS. 1, 2A-2E, and 3. The mask foot boundaries would be defined according to anatomic landmarks similar to the process describe in connection with FIG. 1 above. For full face mask circumferential foot construction, design strategies including two or more zones such as the upper and lower zones described in FIG. 3 could be used to reinforce support not only over the bridge of the nose but along the cheek line where full face mask leaks are likely.

In a working embodiment, a patient specific mask was generated by first taking three photos of the patient's face at different angles. These photos and information therefrom were entered using a Solidworks® software tools to generate a facial rendering. The targeted areas of the patient's face illustrated by the inner borders (114-1 to 114-6) and outer borders (112-1 to 112-6) highlighted in FIG. 1 were then selected for entry as the base topography for the 3D-printer model using standard Stratasys® 3D printer software. Several masks have been built and patient testing showed the prototypes were well tolerated by the patients.

The materials described above are available for use with the Stratasys line of 3D printers and therefore these particular materials were chosen for prototyping and development. However, other materials may be used. Of interest here is that the tissue contacting or tissue-adjacent materials be biocompatible and sufficiently soft and flexible to facilitate patient comfort, with one or more gradients of different materials having distinct material properties defined as the mask foot is built upward, away from the patient tissue, toward a more sturdy and structurally resilient mask body. If desired, at the tissue interface a coating may be applied to enhance patient comfort, for example a thin layer of soft foam.

Figure 5:
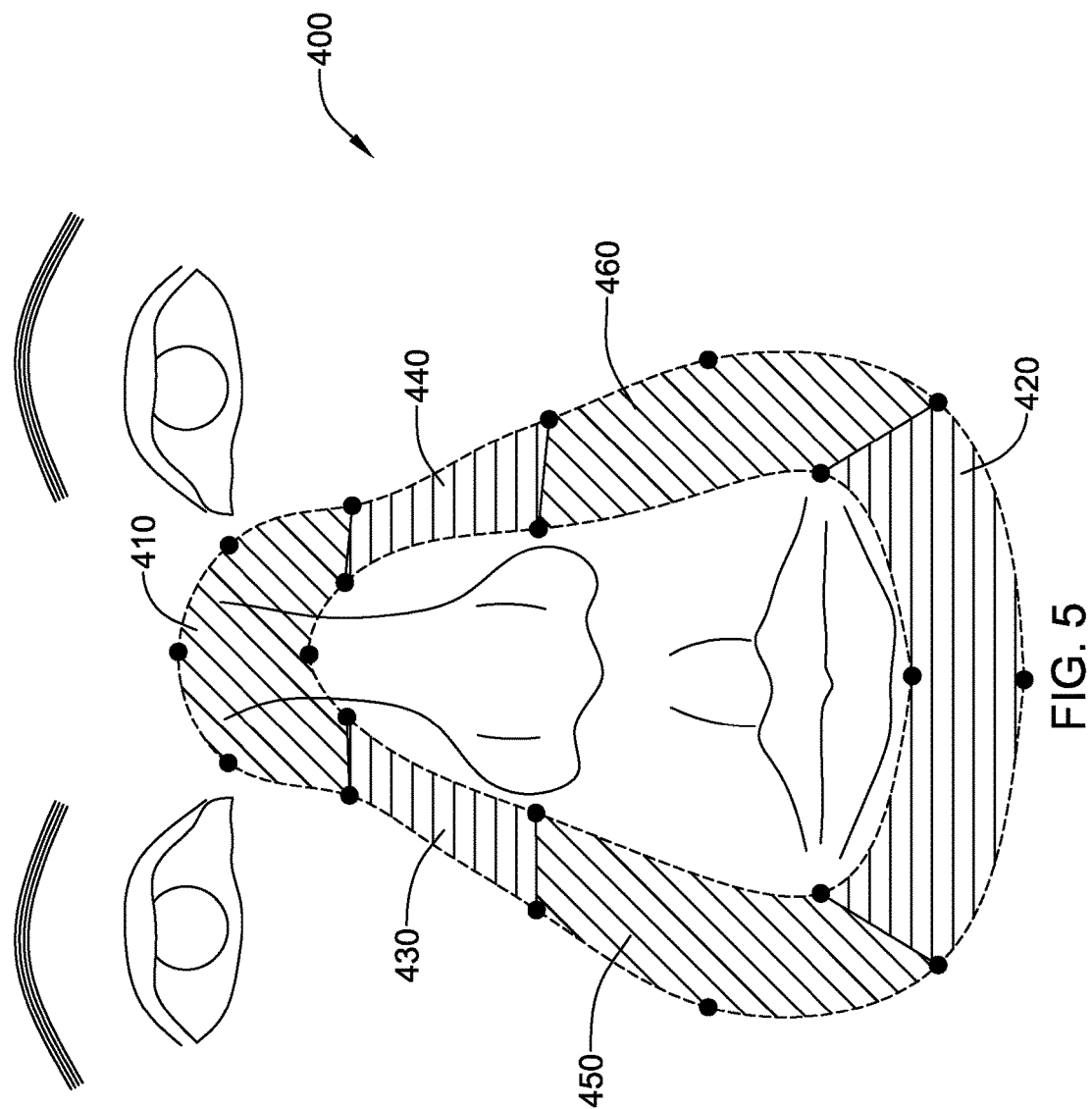
FIG. 5 illustrates a patient wearing a full-face mask.

One example of a mask foot having more than two distinct zones is shown in FIG. 5. Mask foot 400 is characterized by at least four different zone types. Upper zone 410 and lower zone 420 are distinct and separate zones wherein each zone 410, 420 has a different shape, a different material gradient, or both. Zone 430 and zone 440 are different from zone 410 in terms of shape, material gradient, or both. Zones 430, 440 are the same or different in terms of shape, material gradient, or both. Zone 450 and zone 460 are different from zone 420 in terms of shape, material gradient, or both. Zones 450, 460 are the same or different in terms of shape, material gradient, or both. Zone 450 is different from zone 430 in terms of shape, material gradient, or both. Zone 460 is different from zone 440 in terms of shape, material gradient, or both. In some embodiments, zones 430 and 440 are transition zones to transition one or more of material gradient or shape from zone 410 to zones 450 and 460 respectively. In some embodiments, zones 450 and 460 are transition zones to transition one or more of material gradient or shape from zone 420 to zones 430 and 440 respectively.

Figure 6:
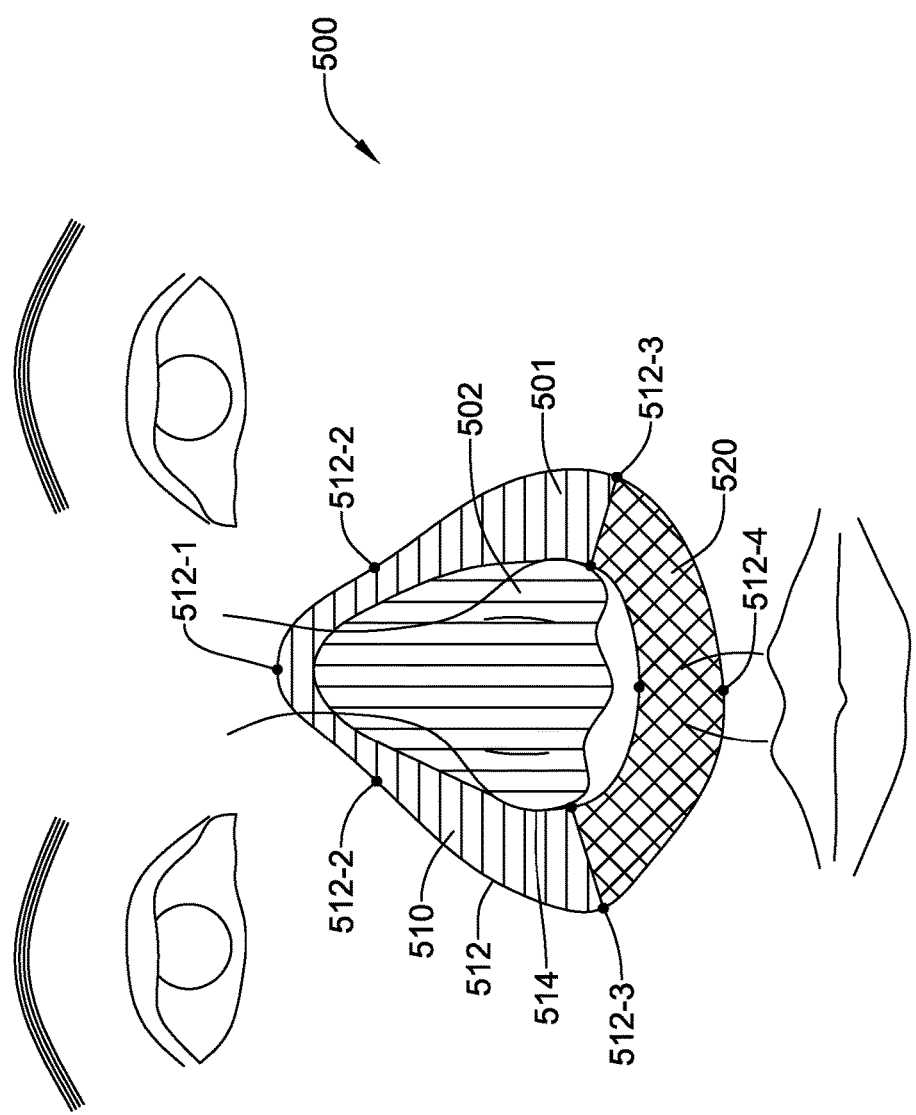
FIG. 6 illustrates a patient wearing another nasal mask.

One example of a "minimalist" mask design that also maximizes pressure distribution and minimizes leaking during contact with the face is shown in FIG. 6. Mask 500 includes mask foot 501 and nose cap 502. Mask foot 501 has first zone 510 and second zone 520; mask foot 501 further has outer boundary 512 and inner boundary 514. Outer boundary 512 is defined by the curved line formed by point 512-1 (approximately 2.4 cm below the nasion), outer boundary points 512-2 (union of nasal and maxillary plains, approximately 1 cm below point 512-1), outer boundary points 512-3 (approximately 1 cm lateral to the alar side walls), and outer boundary point 512-4 (approximately 0.5 cm above the vermilion border at the midline). Inner boundary 514 is defined by the line defined by the alar nasal edge, point 512-1 (midline and approximately 1 mm below the columell-labial angle). Again, the dimensions provided are merely illustrative.

In some embodiments, nose cap 502 rests fully across the surface of the nose. In other embodiments, nose cap 512 partially covers the nose. In some embodiments, nose cap 502 has a wedge shaped cross section, wherein the cap is has a thickness of about 0.5 mm starting near point 512-1 and increasing in thickness as it proceeds in a direction toward outer boundary point 512-4. Maximum wedge thickness of about 3 mm is reached at the alar nasal edge. In some embodiments, nose cap 502 consists essentially of Vero-Clear RGD810 at the non-skin contact surface, consists essentially of TangoPlus FLX930 at the skin contact surface, and includes a material gradient proceeding from the skin contact surface to the non-skin contact surface. The gradient is linear in some embodiments.

At the junction between nose cap 502 and inner boundary 514, a transition gradient (not shown) is provided in a radial direction, that is, the direction proceeding from the edge of the nose cap 502 toward inner boundary 514 over the portion of inner boundary 514 that is connected to the nose cap 502. The transition gradient is determined by the particular material composition at each radial point of connection. In some embodiments, the transition gradient is linear. In other embodiments, the transition gradient is nonlinear, with a greater material ratio change per unit of distance occurring closer to the center of the nose cap 502 and a less material ratio change per unit of distance occurring closer to inner boundary 514.

The design of nose cap 502 provides for contact of the lower half of the nose with the mask foot, resulting in an excellent fit and a much greater area of pressure distribution than previously possible, and thus superior comfort. Meticulous control of material gradients results in superior performance with respect to fit and comfort with minimal leaking.

Second zone 520 is constructed using the mask foot design described in FIG. 3A or FIG. 3C wherein base length 202 (as shown in FIG. 3A) is about 1 cm, height 203 is about 1.0 cm, and apex width 204 is about 0.2 cm. Mask foot second zone 520 further includes a material gradient such as the gradient described in connection with FIG. 3B (the 3D mask foot for which FIG. 3A is a cross sectional view).

Not shown in FIG. 6 is a dome portion of that extends from the edge portion of nose cap 502 not connected to inner boundary 514 (the alar nasal edge) to the inner boundary 514 proximal to lower zone 520. The dome portion may have a uniform thickness throughout. In some embodiments the thickness is in the range of about 1-5 mm, and in one embodiment, about 2 mm. In some embodiments the dome portion is curved over its entirety to smoothly meet the connecting surfaces of the mask foot 501 and nose cap 502. In embodiments, no material gradients are incorporated into the dome portion. A standard tubing port (not shown) may be incorporated into mask 500 in similar fashion to that described for FIG. 4.

Mask 500 provides minimal "dead space" with maximum pressure distribution over the skin while incorporating an excellent fit. The described design elements are obtainable because of seamless gradient designs and meticulous material gradient control.

As previously noted, one or more embodiments of the present invention may provide one or more of improved mask comfort; improved seal for lower leak rates into or out of the mask; less material needed for manufacture than for conventional manufacturing methods; better patient compliance with prescribed therapy for medical masks such as CPAP; customized decoration; no need for facial mold or impressions; and an easy process for both physician and patient; and no need to store inventory.

In some embodiments, a home kit may be designed to allow a patient to take photographs or video at home to enable a distant manufacturing facility to fabricate a CPAP mask. For example, a home kit may include digital cameras disposed in a desired array. In another example, a home kit may include one or more stickers that a user can apply to their face to facilitate imaging by providing fiducials across the patient's face. For example, one or more stickers could be implemented as nasal strips or adhesive bandage-type materials for placement at instructed locations on the patient's face, allowing digital correction of video or still images provided by a patient. As an alternative to a home kit, a physician's office or a sleep clinic may be provided with a photo-booth, an image capture apparatus, or stickers for creating fiducials on the patient's face, to allow the patient to be fitted for a mask in a clinical setting. A mobile solution, such as a van or truck having a suitable setup may also be provided. A web-based system could make use of a patient's webcam by instructing the patient to simply turn their head back and forth a couple of times while the webcam captures video; if the captured video is inadequate, a real-time interface could indicate to the patient what went wrong, if, for example, the patient did not keep their head level or turned too far in one direction. These examples avoid the need to obtain a mold of a patient's face (or part thereof) in order to construct a patient-unique, custom CPAP mask.

Also described herein is a method of fabricating custom made orthotic members, and custom made orthotic members that include one or more material gradients. Orthotics is a specialty within the medical field concerned with the design, manufacture and application of orthoses. An orthosis (plural: orthoses) is "an externally applied device used to modify the structural and functional characteristics of the neuromuscular and skeletal system"—(ISO 8549-1:1989). Orthoses are used in applications including but not limited to: control, guide, limit and/or immobilize an extremities, joint or body segment for a particular reason; to restrict movement in a given direction; to assist movement generally; to reduce weight bearing forces for a particular purpose; to aid rehabilitation from fractures after the removal of a cast; and to otherwise correct the shape and/or function of the body, to provide easier movement capability or reduce pain.

Types of orthoses include, but are not limited to clavicular and shoulder orthoses, arm orthoses, elbow orthoses, arm-wrist orthoses, hand orthoses, foot orthoses (shoe inserts, or insoles), ankle-foot orthoses, knee orthoses, rehabilitation braces and prophylactic braces, spinal orthoses, and the like. In some embodiments, the orthosis is for an animal other than a human; for example, dog and horse orthoses are commonly employed after an injury or to treat a condition in the animal.

It is an advantage of the current methods and articles that each situation is treated with ease both to provide a custom fit of the orthotic member, and to provide material gradients to control pressure distribution during use. Control of pressure distribution is accomplished at the skin/orthotic member interface to result in greater comfort and effectiveness of the orthotic member wherein non-optimized pressure differentials lead to side effects such as soreness, irritation of skin, muscle, tendons, and/or bone, or even bone spurs, tendinitis, bursitis, and the like. The increased comfort experienced by patients when using the custom made orthotic members also leads to greater patient compliance and thus a more effective treatment overall.

One example of a custom made orthotic member is an insole, which is an orthotic member that addresses the plantar area of the foot. A custom made insole that conforms to the shape of the plantar area of the human foot and controls pressure distribution during walking, running, and/or jumping provides for improved fit and greater comfort. As described above, custom manufacturing by additive methods (3D printing), requires less material for manufacture of the orthotic member itself. Additionally, in some embodiments, material gradients are optimized for running or walking or jumping or some other specific mode of movement, for people who engage in activities involving a relatively large proportion of such movement. Examples include but are not limited to long distance running, basketball, cross-country skiing, and the like.

As with the foregoing descriptions, the plantar region of the foot is scanned using digital photos, videos, laser scanning, etc. to generate a computer model of the foot. In some embodiments, scanning of the plantar includes an analysis of pressure points and pressure distribution across the plantar during engagement in certain activities, such as walking or running Such differential pressure is a source of great discomfort to many people. After scanning, the surface of the orthotic member is manipulated to describe a custom fitted orthotic useful as a support device within a shoe or other device such as a brace.

In some embodiments, the insole employs a thin core of stiffer material to support areas of the foot undergoing greater stress during standing, walking or running An example of such a design would be the use of a stiffer materials gradient to support the heel, arch, and metatarsal areas and softer materials gradient for cushioning throughout the remainder of the design.

Figure 7:
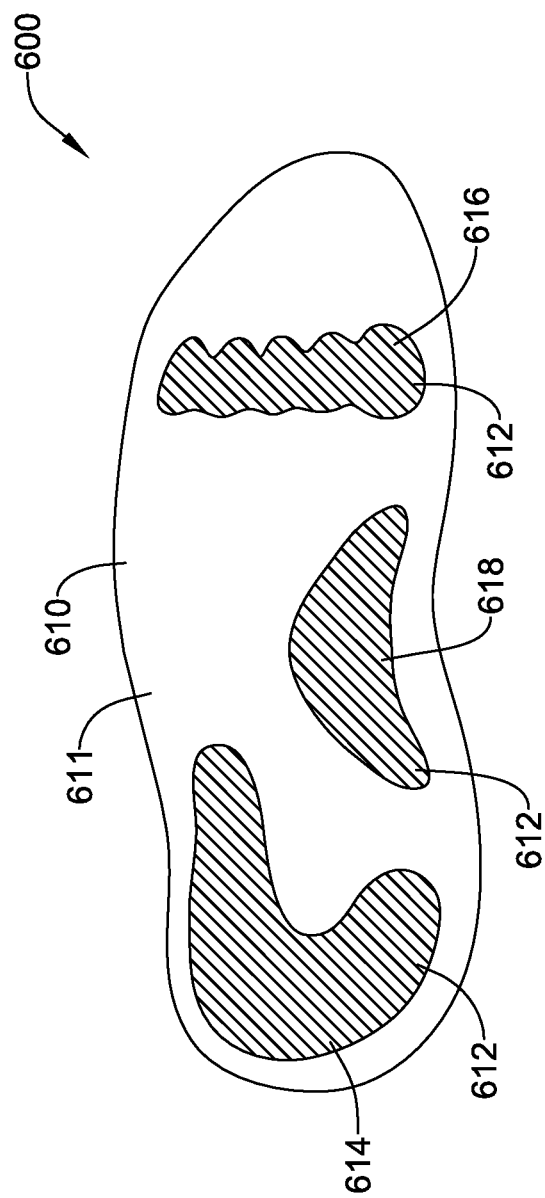
FIG. 7 shows an orthotic embodiment of the present invention.

Referring to FIG. 7, a top view 610 of one example of an insole 600 is shown. By "top view" it is meant that the view shows the side of the insole that would contact a human foot. Insole 410 includes non-gradient portion 611 and gradient portions 612. Gradient portions 612 include heel portion 614, metatarsal portion 616, and arch portion 618. Heel portion 614 and metatarsal portion 616 each include a core region having a non-gradient composition having a first ratio of two polymeric materials, and gradient region surrounding the core region in all directions wherein a linear gradient in polymer ratio proceeds radially to a second ratio of the two polymers at the surface of portions 614, 616. The second ratio is the ratio of polymers present in non-gradient region 611. The gradients and core compositions of heel portion 614 and metatarsal portion 616 are the same or different, in various embodiments.

In one representative embodiment, the core of the heel region 614 and metatarsal region 616 includes a 25/75 (wt/wt) mix of TangoPlus FLX930 and VeroClear RGD810, wherein the cured mixture has a modulus of 1500-1800 MPa. This modulus provides excellent support while being flexible enough to bend slightly with the surface changes required for walking Regions 614, 616 include a 3 mm core region of the 25/75 mixture and include a materials gradient both vertically and horizontally relative to the disposition of insole 600 during use. The vertical gradient of regions 614, 616 extends 2 mm above and below the core region to end at a 75/25 (wt/wt) mix with the surface modulus being approximately 900 MPa. The materials gradient is linear from core region to surface region. This means the majority of the insole 610 will be approximately 7 mm in thickness (defined as the direction perpendicular to the top view as shown), the exception being the arch portion 618 as described below.

Thus, the materials gradient portions 612 at the heel portion 614 and metatarsal portion 616 both include a core region having a 25/75 wt/wt (1800 MPa) ratio of the two polymers described, and transition over a gradient region to a final ratio of 75/25 wt/wt (900 MPa) of the two polymers over a total of 5 mm distance in any direction from the core region. The gradient transition is linear in every direction proceeding from the core regions outward over the gradient regions; that is, the gradient is radial. The non-gradient portion 411 is 75/25 wt/wt of the two polymers, having modulus of 900 MPa throughout. Non-gradient portion 611 is contoured to the plantar of the scanned foot.

Another gradient portion 612 is arch portion 618. Similarly to heel portion 614 and metatarsal portion 616, arch portion 618 includes a core region having a 25/75 wt/wt (1800 MPa) ratio of polymers formed from TangoPlus FLX930NeroClear RGD810, as described above. Dimensions of the core region of arch portion 618 depend on individual anatomy and ranges from about 1 cm to 3.5 cm at its greatest thickness and proceeding an estimated 5-15 cm in length (length defined as the measurement taken from the tips of the toes to the back end of the heel of the foot). The arch portion 618 core region dimensions are defined on three sides by the surface of the foot making contact with the floor and medially by the extension of the line of the arch from a 90 degree overhead view. The gradient region of arch portion 618 proceeding in a direction from the core region of arch portion 618 through the gradient region is 2 mm in all directions. The gradient region of arch portion 618 transitions linearly from a ratio of 75/25 wt/wt (1800 MPa) at the core region to a final ratio of 75/25 wt/wt (900 MPa) of the two polymers. Similarly, the horizontal gradient with be linear over a 5 mm distance in all directions except for medially. The medial gradient will be 2 mm so as to accommodate a better ergonomic fit inside the shoe or other device.

Several of the above examples focus on the use of a gradient within a material blend from a first material composition to a second material transition. In some embodiments, a gradient may be replaced with a lattice, interleaved, or other structure to allow for a gradual transition from one material to another. These lattice and interleaved patterns may be used for a general transition between softer and stiffer materials, such as in a mask foot, or may be used to transition into and away from structural elements such as a frame or backbone for a mask.

Figure 8:
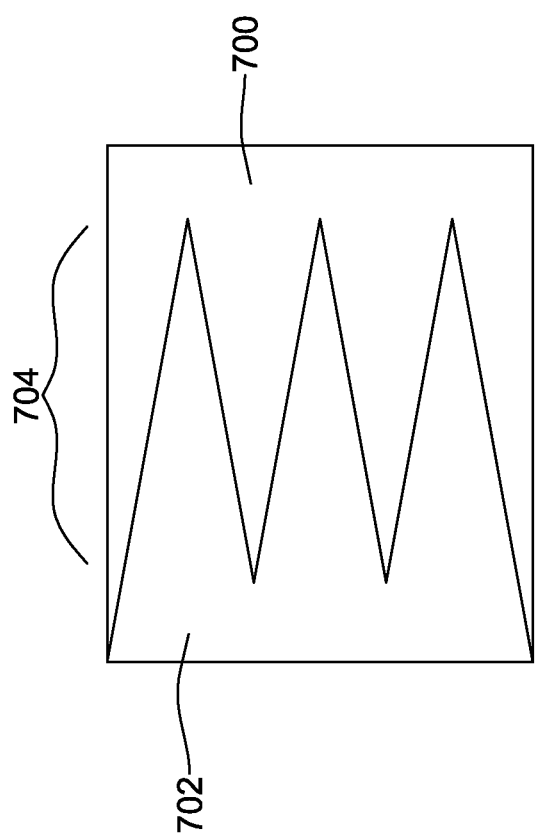
FIG. 8-10 illustrate configurations for varying flexibility of an article.

A first example is shown in FIG. 8, with a transition from a softer material 700 to a harder material 702 across a transition zone 704 characterized by interleaving "teeth". As the cross section occupied by the softer material 700 is reduced and replaced by the harder material 702 as one set of teeth narrows and the other widens, a gradual transition takes place. For the structure in FIG. 8, it may be desirable to also transition the edges of the teeth according to a gradient transition, to avoid the creation of locations of greater stress, strain or fatigue.

Figure 9:
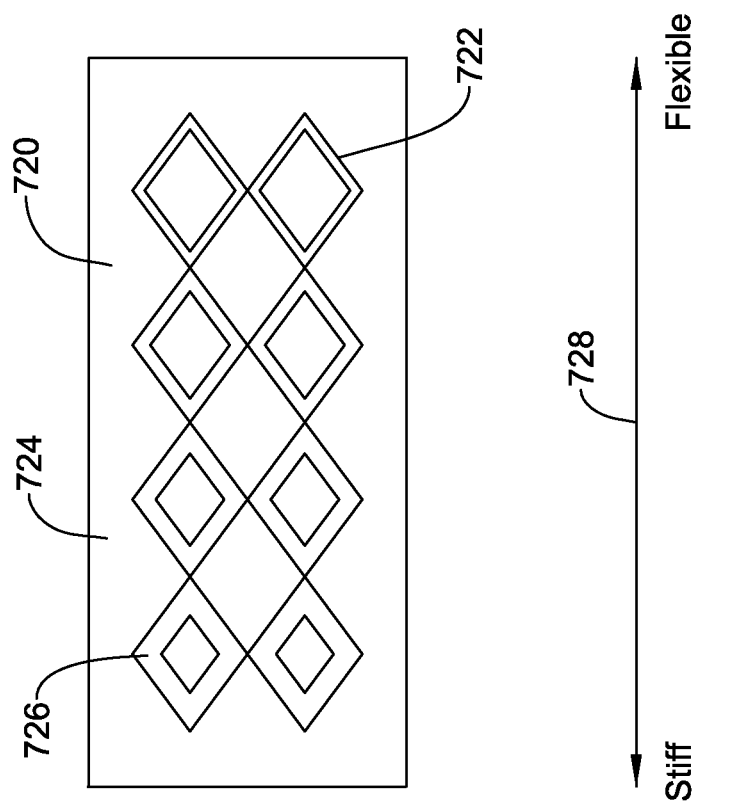

FIG. 9 shows another transition, this time with a piece 720 having a lattice of quadrilaterals 722, 726 of a relatively harder material within a main composition of softer material 724. The thickness of the "beams" of the quadrilaterals changes from thin beams at 722 to thicker beams at 726, imparting a transition from flexible to stiff as illustrated at 728. The lattice structure provides a backbone to the soft material 724, without exposing the edges thereof. A 3D printing process is one very useful way to impart this sort of transition and backbone structure, avoiding the complexity of an insert molding process. Part of the purpose, in this instance, is to enable the benefits of insert molding to be realized without requiring the overhead and process controls associated with a molding process.

Figure 10:
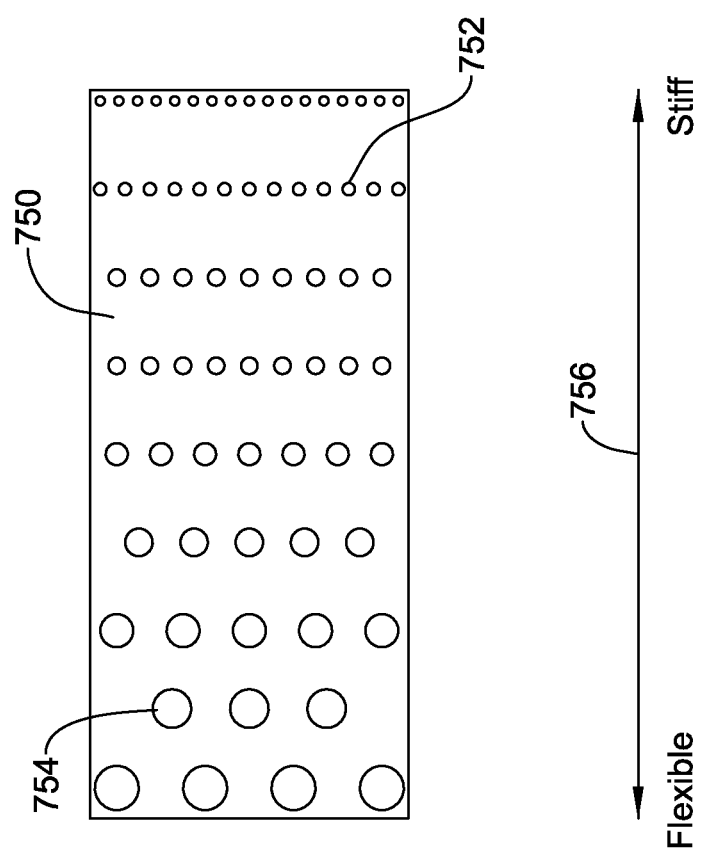

FIG. 10 shows another transition, this time having a background piece 750 of soft material with discs or balls of harder material, with smaller pieces 752 on the right transitioning to larger pieces 754 on the left.

Figure 11:
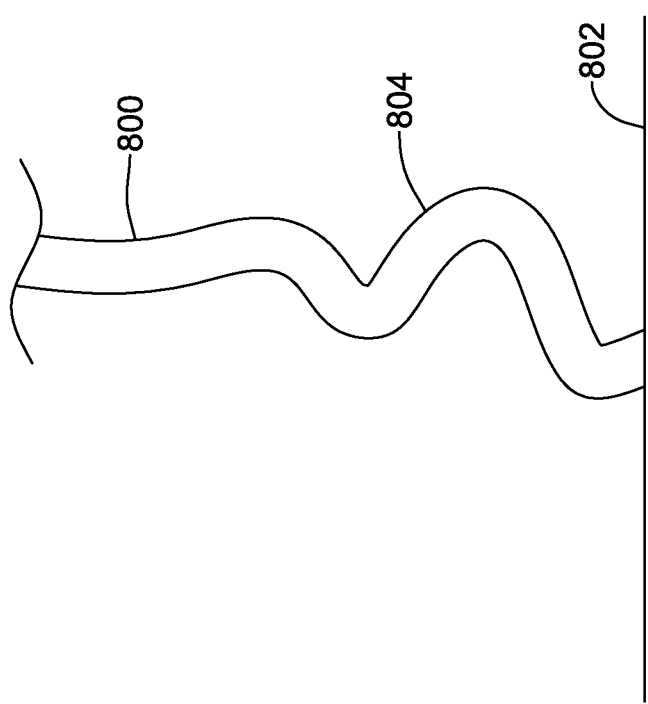
FIGS. 11-12 show illustrative tissue contact designs.
Figure 12:
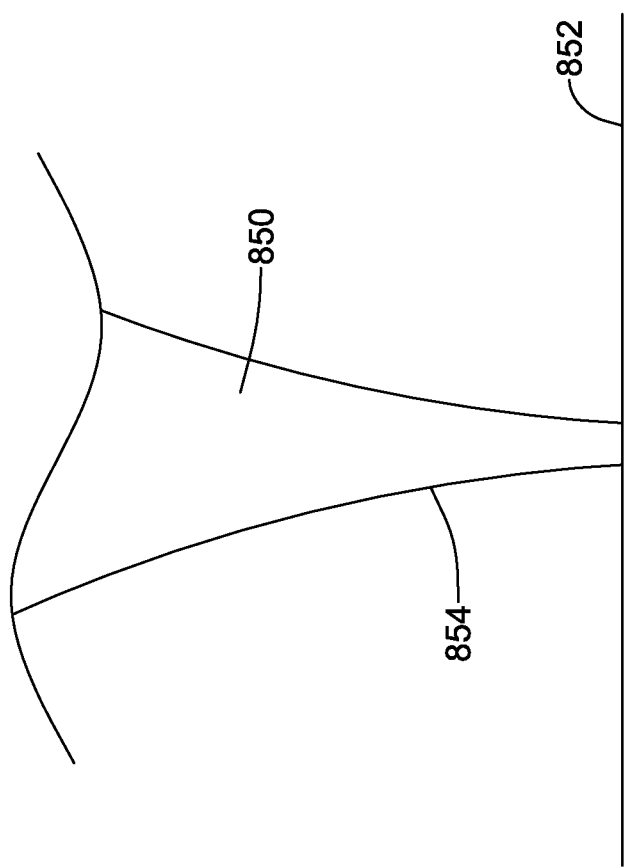

FIGS. 11-12 show illustrative tissue contact designs. In an example shown in FIG. 11, a number of curves are provided as the facial mask 800 come close to the tissue surface 802. The curvatures 804 provide added flexibility and softness, allowing for tissue movement. As noted above, a soft material such as felt or foam may be provided in a thin layer as well to enhance comfort. FIG. 12 shows another example, with a facial mask 850 tapering as it approaches the tissue surface 852 by including a thin region 854. In addition to structurally thinning the material, a gradient may be used here as well. Given the taper to thin region 854, it may be desirable to make the thin region 854 stiffer than the area away from the tissue surface. These examples in FIGS. 11 and 12 may also be used to provide a surface treatment on a mask foot as shown in various of the above examples.

Figure 13:
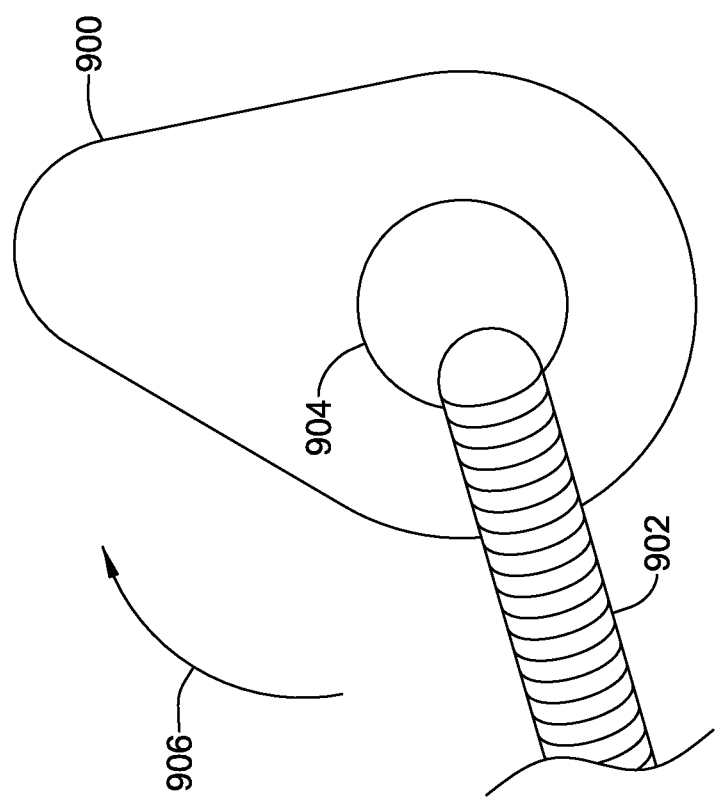
FIG. 13 illustrates a mask having an attachment feature and air tube for coupling to a CPAP machine.

FIG. 13 shows an illustrative mask coupled to an air supply hose using a ball joint. The mask 900 may be a nose cup mask or a full face mask. A coupler 904 connects the hose 902 to the mask 900. The coupler 904 may be attached to the mask by adhesive or bonding, or may be snap fit onto a mask having a built-in connection point (see mask 950 in FIG. 14, below). By using a ball-type coupler 904, the tube 902 can turn about the mask 900 in the direction indicated at 906, allowing the user to move more freely than may be the case with a fixed coupler. Other coupling mechanisms may be used instead.

Figure 14:
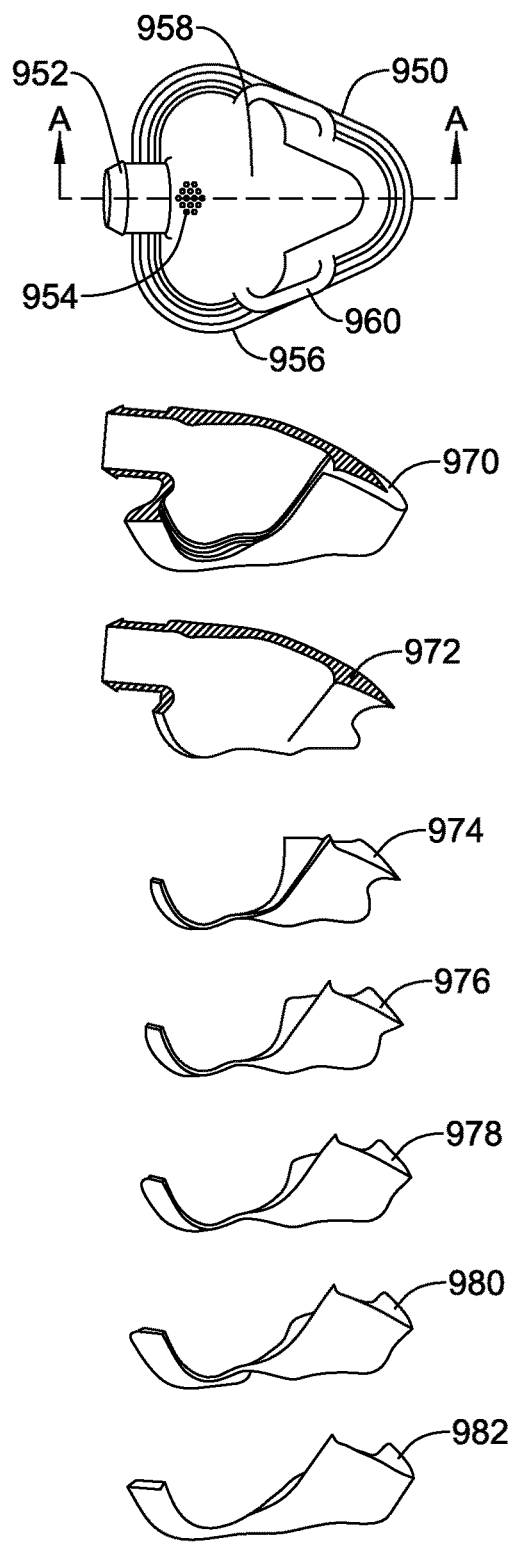
FIG. 14 shows an illustrative working example.

FIG. 14 shows an illustrative working example. A "nose cup" style mask is shown which covers only the patient's nose and forms a seal around it in order to supply air. The individual mask is custom fit to the patient's face. First a computer model of the patient's face is generated using 3D scanning The mask is then idealized by 3D printing with an Objet Connex 3D printer, which has the capability to manufacture objects that have varying material properties within the object.

In the working example, the 3D printer capability is used to construct a mask having a acrylic-like rigid shell which gradually transitions to a softer silicone-like material in the areas of facial contact. By this combination the mask is both rigid enough to hold its shape and flexible enough to be comfortable and adaptable to the wearer's face as it moves. These material transitions take various forms. In the area over the bridge of the nose, the material gradient goes inward from all surfaces, creating a sort of rigid "bone" inside the seal with softer material around it. This allows the seal to be soft enough for comfort and also rigid enough to grip the bridge of the nose for support and positioning. In the area over the upper lip, the gradient goes from soft to rigid straight out from the lip, allowing more flexibility so that the mask can conform more easily to any movements in the patient's lip.

Due to the nature of the computer model used in fabrication of the working embodiment, areas of consistent material properties are defined and provided to the 3D printer as an assembly of layers with incrementally varying rigidity. By using thin layers, a very smooth material transition is obtained.

The finished mask is shown at 950. A tube connector is shown at 952, with adjacent vent holes at 954. In accordance with an embodiment, the region of tissue contact 956 is generally softer and more flexible than the mask cap 958, which defines the volume of air within the mask (also referred to as the dead space), which can be minimized by keeping a generally close fit. Handles 960 are shown for illustrative purpose as well.

A cutaway view along line A-A is shown at 970, and the individually printed layers are shown at 972 to 982. During manufacture, a gradient is formed in small steps with each progressive layer being of a different material composition than a previous layer. For example, the softest, first layer 982 is printed first, followed by a second layer 980 which is slightly softer and formed of a different material composition. The drawing is illustrative in nature; more than the 6 layers shown may be used in some embodiments, with dozens of layers in a single printed article. By using an additive process, each subsequent layer becomes indistinguishable from the prior layer during the process, at least from the perspective the user.

In some embodiments, there is no apparent change when viewed with the naked eye, or when manipulated, as the layers are added one upon another to provide a soft outer surface transitioning to more structured layers and harder elements. Thus, for example, the layer printed at 972 is formed of a hard material that allows for coupling of a tube/hose via a coupler as shown above in FIG. 13, for example, including the snap fit features on the connector 952. One way of describing the structure is that the mask 950 is formed using an additive process in which a first layer, such as layer 982, is suitable to a first purpose (skin/tissue contact) and a second layer, such as layer 972 is suitable to a second purpose (the snap fit coupler), wherein the first layer is poorly suited to the second purpose (as it is too soft) and the second layer is poorly suited to the first purpose (as it is too inflexible), with a gradient transition (such as layers 974, 976, 978 and 980) therebetween which is not perceptible to the naked eye.

FIG. 15 shows an illustrative example of the selecting of inner and outer boundaries based on identified fiducial points. The relative points selected are based on the area around the nose 1000 of a patient. To begin, the edges of the nose are identified with the corners, 1, 2, from which the midpoint 3 can be identified. The base 4 of the nose is identified as well. By choosing the base 4 at the midpoint 3, different shaped noses can be accommodated—it is not simply assumed that the patients nose is a straight line between corners 1, 2. From these fiducial points 1, 2, 3, 4, a set of inner boundaries A, C and E and outer boundaries B, D and F identified.

The method is also shown in block-flow. At block 1010, points 1 and 2 are identified, with point 3 found at 1012. Point 4 is identified at 1014. Next, the inner boundaries A, C and E are set at 1016. Distances A-B, C-D, and E-F are then set, as well as associated angles/vectors for each 1018. For examples, longer or shorter distances can be set taking into account the patients skin texture (oily, dry, wrinkled), the nature of the patient's underskin composition (minimal versus much collagen), with a wider distance used for patient which variable skin—wrinkled, dry skin lacking collagen may call for a wider distance, for example. Some of these factors may be obtained through a patient questionnaire in addition to the use of imaging technology. The angles/vectors used may be, for example, set more horizontally for a patient with a rounder face (as measured by using, for example, the distance from chin to forehead in comparison to the distance between the ears or the outer edges of the eyes, cheek or jawbones) when calculating the nose contours. An additional factor may be the distance from the line 4 to the patient's lips; a narrower distance A-B would be used for a shorter distance to the lips. Then the outer boundaries B, D, and F are set at 1020.

Other measurements that may be incorporated into mask sizing include, for example, the distance between the bilateral crunc lacrum, between bilateral crunc lacrum and the nasion, distance from a point 1 centimeter inferior to the nasion to the bilateral nasal maxillary junction (horizontally), the bilateral distance from the zygomatic arch to the nasal ridge apex (where the point on the zygomatic arch may be defined as directly inferior to the lateral margins of the eyes). In additional examples, the points of interest may include the points on the zygomatic arch directly inferior to the bilateral pupils, then to the nasal ridge apex. In another example, the bilateral points directly inferior to the crunc lacrum and resting over the nasal maxillary junction, including the distance to the nasal ridge apex. Other locations of interest may be defined, with the object of establishing reference points to define the lines and shape thereof for contact surface on the face of a patient.

Figure 16:
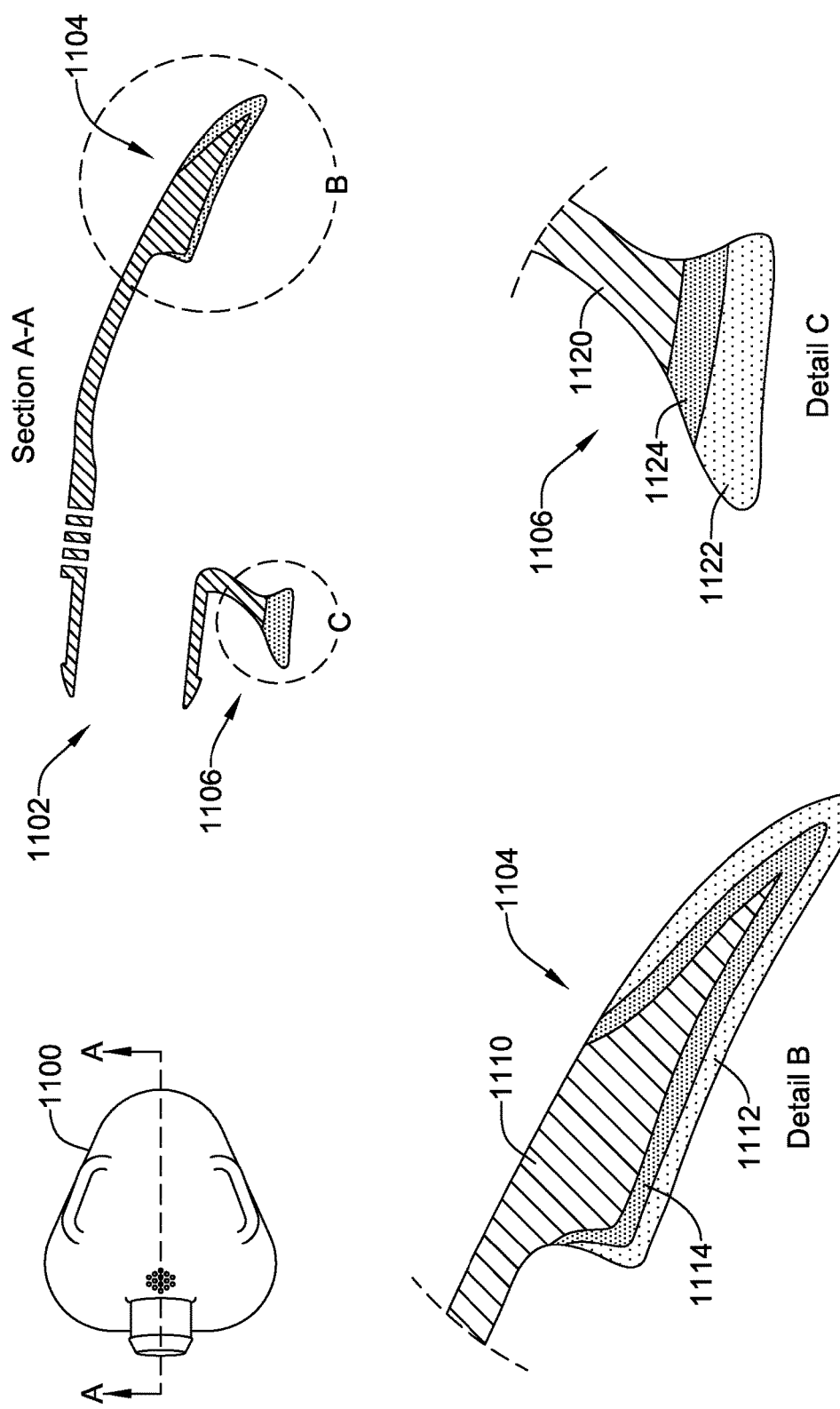
FIG. 16 shows another illustrative working example.

Another illustrative example is shown in FIG. 16, highlighting the use of the gradient structure at the points of skin contact. A mask is shown at 1100, and a section along line A-A is shown at 1102. Further detail views are shown, with B highlighting the structure 1104 for contacting the root and bridge of the nose, and C highlighting the structure 1106 for contacting the philtrum. In the further detail views, structure 1104 includes a soft material at 1112 and a harder structural material 1110 joined together by gradient 1114. Structure 1106 also includes a soft material at 1122 and harder structural material at 1120, joined together by gradient 1124. The soft materials 1112 and 1122 may be similar in composition, or different, if desired. For example, material 1122 may be more flexible than material 1112 in order to accommodate patient mouth/lip movement during sleep. The structural material 1110 and 1120 may be similar or different as well; in an example the two 1110 and 1120 are the same and are generally acrylic.

It should be noted that the addition of color to one or more layers can create a visible transition between layers of different material properties. The intent in several of the embodiments shown above is to provide a smooth transition of material properties. Decorative additions, such as color, should be ignored when contemplating the nature of a transition from one material to another.

Some alternatives may include other breathing support apparatuses such as nasal pillows or a nasal cannula. A nasal pillow may include a cone-shaped outer surface to make contact with the interior of the naris or nostril of a patient. Individual cones or pillows may be designed/shaped by beginning with a scanning technology to obtain a shape of the lower portion of the nose and nasal entrance of the patient. As with the nasal mask approach, a three-dimensional model can be obtained and 3D printing used to realize the design output of the modeling, with softer regions defined at the portions of the nasal pillow which are to contact patient tissue, and a gradient to more rigid materials farther away. The interior of each pillow can be connected to a tube containing pressurized air (for apnea-related uses) or containing therapeutic materials such as oxygen enriched air, nitrous oxide, or an inhalant depending on the needs of a particular application.

For example, a nasal pillow may be designed by obtaining information on the shape and size/location of the naris, the columella, the columella-labial angle and the upper lip to construct custom nasal pillow masks. Such a mask would entail two cone-like surfaces making contact with each naris, with each cone having a circumferential curvature to match each naris, based on the captured images for the patient. Typically each cone may extend into the naris by about 1 to 5 mm, with 3 mm preferred, both horizontally and vertically from the inner naris edge. Each cone could then extend externally to cup the alar and columella portions of each naris in a circumferential manner, again for about 1 to about 5 mm, with 3 mm preferred. Each cone may descend about 3-10 mm, with 5 preferred, to connect to tubing. In an example, a gradient construction would transition from very soft surfaces and edges within the naris to the descending portion of the cones to have a strong structure for tube attachment while being soft at the point of tissue contact. In another example, the gradient structure could connect a very soft material at the skin contact portion of the cone and, over a distance of about 2 mm, to a more rigid material. In one example, the TangoPlus FLX930 material noted above is used at the tissue interface, and a 50/50 mix of FLX930 and VeroClear RGD810 is used for the inner wall of the cone, providing a linear transition from a modulus of 300 MPa at the skin contact to about 1200 MPa in the interior cone wall. A lip foot may be added as well to link the two nasal pillows and allow the mask to rest on the upper lip of the patient.

Another illustrative example takes the form of a nasal cannula. By observing the anatomic surfaces of the patient and using 3D printing with gradient technology as described above, a nasal cannula for delivery of breathable oxygen may be provided. Using a digital or other image or 3D scan of the lower portion of the nasal entrance, the shape of each naris, the columella, the contours of the naris-labial junction, and the basilar inlet of each naris may be obtained. This topography would then be used to print a nasal cannula for smooth and gentle contact with the nasal inlet and upper lip of the patient. Such a cannula design may be constructed to occupy about 25-33% of the cross-sectional area of each naris inlet.

An inner portion of such a nasal cannula can include an oxygen port of about 3 mm diameter, which is similar to existing equipment. The rounded inner portion would use a harder material (such as the 50/50 blend of FLX930 and RGD810 noted above), and changes across a gradient to the outer, tissue contacting portion of the cannula to a softer material (such as a 100% FLX930 material). Each cannula may be approximately 5-15 mm long (with 10 mm preferred), and 3-7 mm wide (with 5 mm preferred), though such dimensions may also be customized. The cannulas may extend into the naris for about 3-6 mm, with 4 mm preferred. The oxygen ports may be rounded to avoid irritation inside the nose, and another gradient may be used from the tip to the interior of the cannula to assist with reducing irritation. Upon exiting each naris, the cannula can bend in the range of 25 to 60 degrees, or more likely 34-45 degrees to align with the naris-labial junction.

The area of tubing between and connecting to each oxygen port of such cannulas can be contoured to the shape of the patient's anatomy at the base of the columella and columella-labial angle. The ports may be in the range of 3-8 mm apart. The cannula can then be attached to standard tubing.

Because 3D printing can be used on-site to make a specialized nasal pillow and/or nasal cannula, more comfortable and secure placement can be obtained for example in the hospital where some such devices are commonly used, without requiring a wide variety of shapes and sizes to be maintained in stock.

Each of these non-limiting examples can stand on its own, or can be combined in various permutations or combinations with one or more of the other examples. The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or aspect thereof), either with respect to a particular example, or with respect to other examples shown or described herein. In the event of inconsistent usages between this document and any document incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

The invention illustratively disclosed herein can be suitably practiced in the absence of any element which is not specifically disclosed herein. While the invention is susceptible to various modifications and alternative forms, specifics thereof have been shown by way of examples, and are described in detail. It should be understood, however, that the invention is not limited to the particular embodiments described. On the contrary, the intention is to cover modifications, equivalents, and alternatives falling within the spirit and scope of the invention. In various embodiments, the invention suitably comprises, consists essentially of, or consists of the elements described herein and claimed according to the claims.

What is claimed:

1. A facial mask comprising a first material and a second material and a first material gradient in at least a portion of the mask, the first material gradient transitioning from the first material to the second material;
   wherein the first material is a relatively softer material well suited to contact with the face of a patient, and the second material is a harder material well suited to providing a structure and shape to the mask;
   wherein the mask is made by additive manufacturing in which the first material is deposited in a first layer, and the second material is deposited in a second layer, with blends of the first and second materials deposited in intermediate layers, the intermediate layers providing the first gradient, without the use of insert molding or casting;

further wherein the blends of the first and second materials are formed prior to deposition according to mixing ratios that are adjusted as the intermediate layers are deposited;

wherein the mask comprises a first zone (310) shaped to place over the bridge of the patient's nose, and a second zone (320) shaped to place over the nostrils and/or mouth of the patient, with a second material gradient (330) therebetween, wherein the second material gradient provides a transition between the first zone and the second zone in which the first zone comprises a core skeleton element, the second zone omits the core skeleton element, and the second gradient transitions from inclusion of the core skeleton element at the first zone to absence of the core skeleton element in the second zone;

wherein the first material gradient and the second material gradient are characterized by a lack of discernable boundary insofar as there is no visible boundary to the naked eye and insofar as a boundary cannot be identified under manual inspection.

2. The facial mask of claim 1 wherein the first material is a polymeric material suited to a first purpose, and the second material is a polymeric material suited to a second purpose and not to the first purpose.

3. The facial mask of claim 1 wherein the first and second materials differ in one or more of modulus, elasticity, glass transition temperature, degree of crystallinity, ductility, softening point, or melt flow index.

4. The facial mask of claim 1 wherein the mask is a CPAP mask.

* * * * *